US009977136B2

(12) United States Patent
Barrett et al.

(10) Patent No.: US 9,977,136 B2
(45) Date of Patent: May 22, 2018

(54) BETA AND ALPHA EMISSION TOMOGRAPHY FOR THREE-DIMENSIONAL AUTORADIOGRAPHY

(71) Applicants: Arizona Board of Regents on Behalf of The University of Arizona, Tucson, AZ (US); inviCRO, LLC, Boston, MA (US)

(72) Inventors: Harrison H. Barrett, Tucson, AZ (US); Brian Miller, Tucson, AZ (US); Yijun Ding, Aurora, CO (US); Liying Chen, Redmond, WA (US); John William Hoppin, Boston, MA (US); Luca Caucci, Tucson, AZ (US)

(73) Assignees: The Arizona Board of Regents on Behalf of The University of Arizona, Tucson, AZ (US); inviCRO, LLC, Boston, MA (US)

( * ) Notice: Subject to any disclaimer, the term of this patent is extended or adjusted under 35 U.S.C. 154(b) by 0 days. days.

(21) Appl. No.: 15/729,428

(22) Filed: Oct. 10, 2017

(65) Prior Publication Data

US 2018/0052242 A1    Feb. 22, 2018

Related U.S. Application Data

(62) Division of application No. 15/116,173, filed as application No. PCT/US2015/014223 on Feb. 3, 2015, now Pat. No. 9,823,364.

(Continued)

(51) Int. Cl.
*G01T 1/29*    (2006.01)
*G01T 5/08*    (2006.01)
(Continued)

(52) U.S. Cl.
CPC ............ *G01T 1/2942* (2013.01); *A61B 6/037* (2013.01); *A61B 6/4258* (2013.01);
(Continued)

(58) Field of Classification Search
CPC ..... A61B 6/037; A61B 6/4258; A61B 6/5205; G01T 1/161; G01T 1/2942; G01T 1/2985; G01T 5/08
See application file for complete search history.

(56) References Cited

U.S. PATENT DOCUMENTS 5,376,800 A    12/1994    Solares et al.
7,928,397 B2    4/2011    Barret et al.
(Continued)

FOREIGN PATENT DOCUMENTS

WO    WO 2010/025300    3/2010
WO    WO 2013/186798    12/2013

OTHER PUBLICATIONS

Bashkirov et al. (2008) "Experimental Verification of Track Structure Models," 2008 IEEE Nuclear Science Symposium Conference Record. pp. 2890-2894.
(Continued)

*Primary Examiner* — Mark R Gaworecki
(74) *Attorney, Agent, or Firm* — Lathrop Gage LLP

(57) ABSTRACT

The present invention provides methods and systems for 3D imaging of in vivo and ex vivo tissues. The disclosed systems and methods employ an autoradiographic approach where particles emitted by a radioactive composition within the tissue are detected. Once detected, a 3D representation of the source of particles within the tissue is reconstructed for viewing and analysis.

20 Claims, 21 Drawing Sheets

Related U.S. Application Data

(60) Provisional application No. 62/078,580, filed on Nov. 12, 2014, provisional application No. 61/934,990, filed on Feb. 3, 2014.

(51) Int. Cl.
  *A61B 6/03* (2006.01)
  *G01T 1/161* (2006.01)
  *A61B 6/00* (2006.01)

(52) U.S. Cl.
  CPC ............ *A61B 6/5205* (2013.01); *G01T 1/161* (2013.01); *G01T 1/2985* (2013.01); *G01T 5/08* (2013.01)

(56) References Cited

U.S. PATENT DOCUMENTS

| | | |
|---|---|---|
| 8,519,338 B2 | 8/2013 | Barret et al. |
| 2004/0015075 A1 | 1/2004 | Kimchy et al. |
| 2009/0133167 A1 | 5/2009 | Yakushevska et al. |
| 2011/0084212 A1 | 4/2011 | Clark |
| 2011/0220802 A1 | 9/2011 | Frisch et al. |
| 2011/0248163 A1 | 10/2011 | Morris et al. |
| 2011/0249866 A1 | 10/2011 | Pietsun et al. |
| 2012/0056104 A1 | 3/2012 | Perna |
| 2012/0168630 A1 | 7/2012 | Beddar et al. |

OTHER PUBLICATIONS

Chen et al. (2009) "Direct charged-particle imaging system using an ultra-thin phosphor: physical characterization and dynamic applications," IEEE Trans Nucl Sci. 56(5):2628-2635.

Miller (2011) "High-Resolution Gamma-Ray Imaging with Columnar Scintillators and CCD/CMOS Sensors, and FastSPECT III: A Third-Generation Stationary SPECT Imager," Dissertation, the University of Arizona.

Miller et al. (2007) "Gamma-ray microscopy using micro-coded apertures and Bazooka SPECT, a low-cost, high resolution image intensifying gamma camera," J Nucl Med. 48(Suppl 2):47P.

Miller et al. (2008) "Recent advances in BazookaSPECT: Real-time data acquisition and the development of a gamma-ray microscope," Nucl. Inst. Meth. Phys. Res. A. 591(1):272-275.

Miller et al. (2009) "Progress in BazookaSPECT," Proc. SPIE. 7450:7450C.

Miller et al. (2009) "System integration of FastSPECT III, a dedicated SPECT rodent-brain imager based on BazookaSPECT detector technology," IEEE Nucl. Sci. Symp. Conf. Record. pp. 4004-4008.

Miller et al. (2012) "Progress in BazookaSPECT: high-resolution dynamic scintigraphy with large-area imagers," Proc. SPIE. 8508:85080F.

Miller et al. (Dec. 11, 2014) "The iQID camera: An ionizing-radiation quantum imaging detector," Nucl Instrum Methods Phys Res A. 767:146-152.

Miller et al. (Jul. 2015) "Quantitative single-particle digital autoradiography with α-particle emitters for targeted radionuclide therapy using the iQID camera" Med Phys. 42(7):4094-4105.

Parra et al. (1998) "List-mode likelihood—EM algorithm and noise estimation demonstrated on 2D-PET," IEEE Trans Med Imaging. 17(2):228-235.

European Supplemental Search Report corresponding to European Patent Application No. 15783103.3, dated Sep. 11, 2017.

International Search Report with Written Opinion corresponding to International Patent Application No. PCT/US2015/014223, dated Jan. 27, 2016.

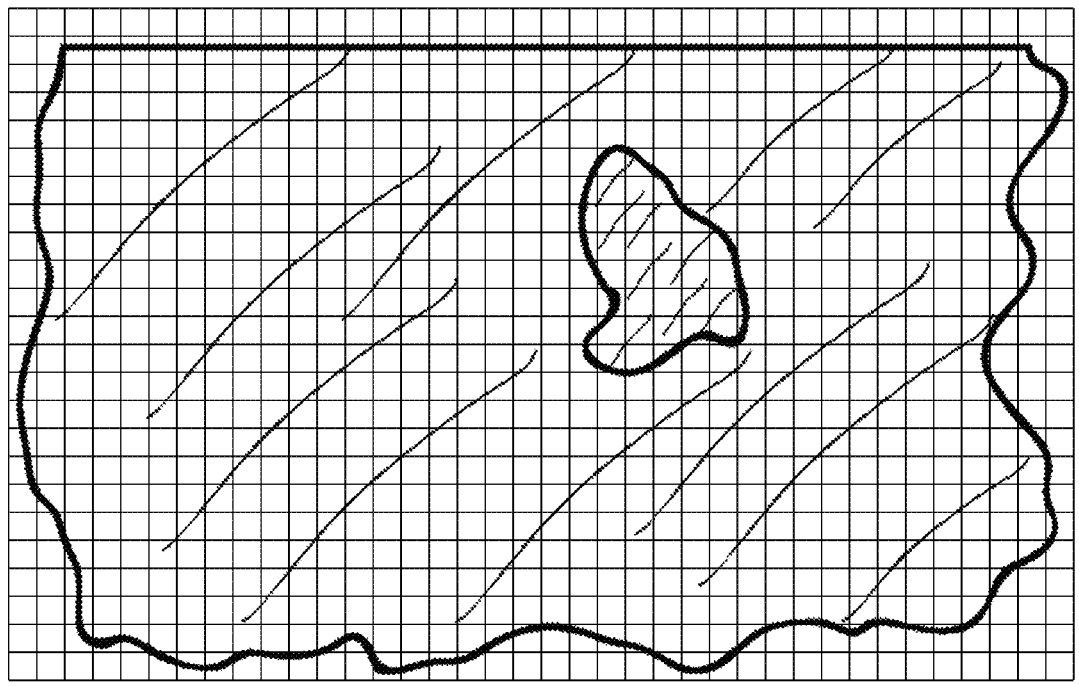
FIG. 6a
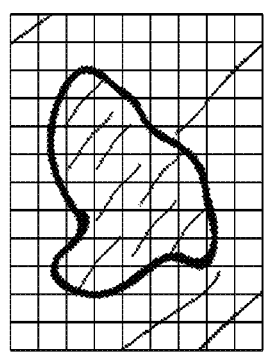 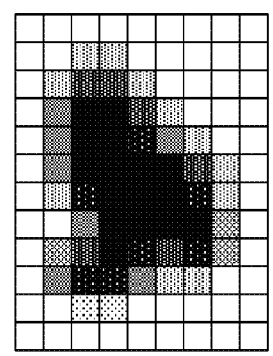
FIG. 6b     FIG. 6c

BETA AND ALPHA EMISSION TOMOGRAPHY FOR THREE-DIMENSIONAL AUTORADIOGRAPHY

CROSS-REFERENCE TO RELATED APPLICATIONS

This application is a divisional of U.S. patent application Ser. No. 15/116,173, filed Aug. 2, 2016, which is U.S. National Stage Application under 35 U.S.C. § 371 of International Application No. PCT/US2015/014223, filed Feb. 3, 2015, which claims the benefit of priority from U.S. Provisional Patent Application Nos. 61/934,990 filed Feb. 3, 2014, and 62/078,580 filed Nov. 12, 2014, each of which is hereby incorporated by reference in its entirety to the extent not inconsistent herewith.

STATEMENT REGARDING FEDERALLY SPONSORED RESEARCH OR DEVELOPMENT

This invention was made with governmental support under Grant Nos. P41 EB002035 and R01 EB000803, awarded by NIH. The government has certain rights in the invention.

BACKGROUND

Autoradiography is a well-developed technique for imaging in the context of clinical medicine and research on biological processes. In this technique, a radioactive probe is administered to a patient or a subject or a tissue to provide an internal source of radiation, thus distinguishing this method from conventional radiography in which an external source of radiation is employed. Autoradiography is most commonly used for imaging of ex vivo samples obtained from tissue administered with a radioactive pharmaceutical. Thin slices (e.g., 5-50 µm thick) of the sample are subsequently analyzed using a high-resolution imaging detector sensitive to charged particles (e.g., alpha particles, beta particles and/or Auger electrons) emitted by the radioactive pharmaceutical. These techniques provide 2D images exhibiting high spatial resolution capable of resolving the distribution of a radioactive pharmaceutical at the cellular or subcellular level.

Although autoradiography provides a valuable approach for high-resolution imaging of tissue, this technique is significantly limited in its extension to 3D imaging of in vivo tissue. While reassembly of 2D slice image information to obtain a 3D image of a sample is feasible, this application of autoradiography is labor intensive and practically limited due to distortion of thin film slices introduced by dehydration and/or in transferring them to an imaging detector. Further, extension of conventional autoradiography to 3D imaging requires sectioning of the sample into thin slices to provide depth information, thereby effectively limiting the technique to application of ex vivo tissue samples.

SUMMARY

The present invention provides autoradiography methods and devices for 3D imaging via the detection of beta particles, alpha particles or other charged particles. Embodiments of the present methods and systems provide high-resolution 3D imaging of the distribution of a radioactive probe, such as a radioactive pharmaceutical, in an intact, unsectioned tissue sample without the need for physically slicing the sample into sections. Embodiments of the present methods and systems provide for 3D imaging of in vivo tissue and ex vivo tissue via detection of particles from a single side of the sample. Embodiments of the present methods and systems provide for 3D imaging of living tissue including, for example, dynamic, time evolved imaging and characterization of a living tissue sample.

The disclosed systems and methods employ an autoradiographic imaging approach where particles emitted by a radioactive composition within the tissue are detected to provide a plurality of position dependent signals, for example, providing information characterizing individual trajectories of the detected particles. In some embodiments, a charged particle track detector is used to independently detect particles at a plurality of positions along their respective trajectories. For example, suitable track detectors include scintillator-based detectors, microchannel plate-based image intensifiers coupled to a thick scintillation material or a CCD or other video camera type detector where the sensitive region, active region or depletion region is thick enough to stop the particle. The recorded track can be analyzed to determine features of each track such as the point at which the charged particle entered the thick detector, the particle's direction at that point and the total energy deposited in that track. In embodiments, these features are used in an iterative tomographic reconstruction algorithm for accurate determination of a 3D image of the distribution of the source of particles within the tissue, for example, by determining positions and directions of the detected particles interacting with a charged particle track detector. In embodiments, characterization of the positions and directions of particles entering a detector provides information useful for determining a distribution of the source of particles within the tissue using various methods. In some embodiments, a particle transport algorithm is utilized, which estimates, simulates or otherwise accounts for propagation processes that take place between a location and the point at which the particle interacts with the detector. In some embodiments, for example, a maximum likelihood expectation maximization algorithm is used to accurately reconstruct a 3D image of the distribution of a radiopharmceutical in a sample from the position dependent signals collected for the detected particles. Optionally, the devices and methods of the invention are useful for not only detecting beta particles and alpha particles, but other energetic particles, including conversion electrons, auger electrons, electron-like particles and/or positrons.

In a first aspect, provided are methods for imaging a source of particles, such as beta particles, alpha particles or conversion electrons. In an embodiment, methods of this aspect are also useful for reconstructing a 3D distribution of a source of the particles. In a specific embodiment, a method of this aspect comprises the steps of: repeating, for each of a plurality of particles from the source, the steps of: a) recording an image of a particle track with a particle track detector; b) determining attributes of the particle track using the particle track image; and c) storing the attributes of the particle track; thereby generating attributes for each of the plurality of particles from the source; and reconstructing a 3D distribution of the source of particles using the attributes for each of the plurality of particles. In an embodiment, for example, the method of the invention further comprises the step of storing the attributes as entries in an attribute list, 4D grid or database. In an embodiment, the attributes of the particle track are determined to within the uncertainty of a selected analytical approach, such as a list-mode maximum likelihood expectation-maximization algorithm. In an embodiment, the attributes of the particle track are estimated, for example, using an approximate analysis technique or predictive algorithm.

In an embodiment, a further method of this aspect comprises the steps of: detecting a plurality of particles from the source by measuring first and second position dependent signals for each detected particle; analyzing the first and second position dependent signals for each detected particle to determine at least one position and at least one direction characterizing each particle's independent particle trajectory; and reconstructing a 3D image of the source of particles using the positions and directions characterizing the independent particle trajectories of the detected particles. In embodiments, each detected particle traverses an independent particle trajectory. In embodiments, the first and second position dependent signals correspond to first and second points along the independent particle trajectory of each detected particle.

Use of detector techniques that are substantially transparent to the detected particles is useful in some embodiments of the invention. In an embodiment, for example, the step of detecting a plurality of particles by measuring first and second position dependent signals for each detected particle does not significantly change the trajectory of the detected particles. In an embodiment, for example, the step of detecting a plurality of particles by measuring first and second position dependent signals for each detected particle does not substantially result in scattering of the detected particles.

In an exemplary embodiment, the step of detecting a plurality of particles comprises interacting each detected particle with an active material of a charged particle track detector positioned to intersect at least a portion of the independent particle trajectory of each detected particle, thereby generating the first and second position dependent signals. In an embodiment, for example, the active material comprises a scintillator, a microchannel plate or a depletion region of a deep-depletion CCD device or deep-depletion CMOS device.

In an embodiment, for example, methods of this aspect utilize a scintillator to detect particles. Scintillation-based detection methods are useful, for example, as two-dimensional detection of electromagnetic radiation generated by interactions between a particle and a scintillator can be achieved using a variety of detectors, such as a CCD detector or other kind of cameras. In addition, scintillation-based detectors optionally provide for techniques that determine a location of a particle in three dimensions as well as an absolute direction of travel of a particle, such as three dimensions describing the point at which the particle interacts with an active material of a detector, such as a thick scintillator or a first of a plurality of thin scintillator foils. This information, as described above, is useful for determining the distribution of a source of particles. Scintillation-based detection methods also enable distinguishing between separate particles detected simultaneously or within a short time of one another, such as within 100 µs of one another. In embodiments, continuously updated sources of images, such as from a frame based integrating detector, for example a CCD camera, are useful for simultaneously detecting spatially resolved tracks from multiple particles at once. Optionally, the decay time of a particle in the active material is smaller than the frame time, such that a track of the particle can be recorded in a single frame. In embodiments, tracks of multiple particles are recorded in a single frame.

Scintillator-based detection is useful in certain embodiments for providing position dependent characterization of particle trajectories. In a specific embodiment, the step of detecting a plurality of the particles comprises the steps of: interacting each detected particle with a scintillator positioned to intersect at least a portion of the independent particle trajectory of each detected particle, where the interaction between a particle and the scintillator generates the first and second position dependent signals corresponding to electromagnetic radiation generated at first and second points along a particle's track, such as a portion of the independent particle trajectory of each detected particle in the scintillator; and detecting at least a portion of electromagnetic radiation using a two-dimensional optical detector. In a specific embodiment, a particle track detector comprises a scintillator positioned proximate to the source of particles and a two-dimensional optical detector positioned in optical communication with the scintillator; wherein each particle track that is imaged corresponds to a particle path within the scintillator. In an embodiment, for example, a step of a method of recording an image of a particle track with a particle track detector comprises: interacting a particle with a scintillator positioned proximate to the source, wherein the interaction generates a detectable optical signal along the particle track within the scintillator; and detecting at least a portion of the optical signal using a two-dimensional optical detector.

In an embodiment, for example, the scintillator has a thickness selected from the range of 3 µm to 3 mm. In an embodiment, for example, the scintillator comprises a first scintillator foil and a second scintillator foil. In embodiments, the first point is located in the first scintillator foil and the second point is located in the second scintillator foil. In embodiments, for example, the first scintillator foil and the second scintillator foil are separated by a distance selected from the range of 10 µm to 1 mm. In an embodiment, for example, the first scintillator foil and the second scintillator foil independently have thicknesses selected from the range of 3 µm to 100 µm. In embodiments, the first scintillator foil and the second scintillator foil independently comprise one or more materials selected which generate light when a charged particle interacts with the materials, such as, for example, ZnO or $Gd_2O_2S$. In an embodiment, for example, the first scintillator foil and the second scintillator foil independently comprise doped materials, for example materials including a dopant such as Er, Ga, In. In exemplary embodiments, the first scintillator foil and the second scintillator foil independently comprise one or more of YaG:Ce, LAG:Eu and GGG:Eu.

In an exemplary embodiment, a method of this aspect further comprises the step of imaging the electromagnetic radiation (i.e., light) from the scintillator onto the two-dimensional optical detector using a lens or lens system. In an embodiment, for example, the two-dimensional optical detector comprises a charge-coupled device (CCD) detector or detector array, a complementary metal-oxide-semiconductor (CMOS) detector or detector array, a metal-oxide-semiconductor (MOS) detector or detector array or an active pixel sensor or array of active pixel sensors. In an embodiment, for example, the two-dimensional optical detector collects images at a frame rate of 10000 frames per second or greater. Optionally, particle tracks of multiple particles are recorded within a single frame or image of the two-dimensional optical detector. In an embodiment, for example, the two-dimensional optical detector collects data from $10^{10}$ detector elements per second or greater. Optionally, particle tracks of multiple particles are recorded simultaneously by a particle track detector.

Microchannel plate-based detection is useful in certain embodiments for providing position dependent characterization of particle trajectories. In an embodiment, for example, methods of this aspect utilize a microchannel plate to detect particles. Detection methods employing microchannel plates are useful, for example, as two-dimensional detection of electromagnetic radiation generated by interactions between a particle and a microchannel plate can be achieved using a variety of detectors. In addition, microchannel plate based detectors optionally provide for techniques that determine a location of a particle in three dimensions as well as an absolute direction of travel of a particle. This information, as described above, is useful for determining a 3D distribution of the source of particles. Detection methods employing microchannel plates also enable distinguishing between separate particles that are detected simultaneously and/or within a single frame of an imaging system but generate spatially separated tracks.

In a specific method embodiment of this aspect, the step of detecting at least a portion of the particles comprises the steps of: interacting each detected particle with a microchannel plate positioned to intersect at least a portion of the independent particle trajectory of each detected particle, where the interaction generates the first and second position dependent signals corresponding to electrons generated at the first and second points along the independent particle trajectory of each detected particle in the microchannel plate; amplifying the generated electrons in the microchannel plate and directing the amplified electrons into a phosphor layer adjacent to the microchannel plate, where the amplified electrons generate electromagnetic radiation upon interaction with the phosphor layer; and detecting at least a portion of electromagnetic radiation using a two-dimensional optical detector. In a specific embodiment, a particle track detector comprises a microchannel plate positioned proximate to the source of particles, a light-emitting material positioned proximate to the microchannel plate and a two-dimensional optical detector positioned in optical communication with the light-emitting material; wherein each particle track corresponds to a particle path within the microchannel plate. In an embodiment, for example, a step of recording an image of a particle track with a particle track detector comprises: interacting a particle with a microchannel plate positioned proximate to the source, wherein the interaction generates electrons along the particle track within the microchannel plate, wherein the generated electrons are amplified within the microchannel plate and directed onto a light-emitting material positioned proximate to the microchannel plate, wherein interactions between the electrons and the light-emitting material generate a detectable optical signal; and detecting at least a portion of the detectable optical signal using a two-dimensional optical detector.

For certain embodiments, the first and second position dependent signals are independently amplified by the microchannel plate. For example, in an embodiment, the amount of amplification of the first and second position dependent signals or detectable electrons generated along a particle track depends on the position of the first and second points or particle track in the microchannel plate. In embodiments, for example, an amount of electromagnetic radiation generated by the phosphor layer or light-emitting material is proportional to the amplified amount of signal generated by the microchannel plate. Such a configuration optionally permits independent detection and identification of the first and second position dependent signals by the two-dimensional optical detector, providing the ability to distinguish the position and location of each of the first and second points or the ability to determine the position of a particle track in the microchannel plate.

In an embodiment, for example, methods of this aspect further comprise the step of imaging the electromagnetic radiation from the phosphor layer onto the two-dimensional optical detector using a lens or lens system. In a specific embodiment, the two-dimensional optical detector comprises a charge-coupled device (CCD) detector or detector array, a complementary metal-oxide-semiconductor (CMOS) detector or detector array, a metal-oxide-semiconductor (MOS) detector or detector array, an active pixel sensor or sensor array. In an embodiment, for example, the two-dimensional optical detector collects images at a frame rate of 10000 frames per second or greater. In an embodiment, for example, the two-dimensional optical detector collects data from $10^{10}$ detector elements per second or greater. Optionally, particle tracks of multiple particles are recorded simultaneously by a particle track detector.

Deep-depletion charge coupled device-based detection or deep-depletion CMOS-based detection is useful in certain embodiments for providing position dependent characterization of particle trajectories. In an embodiment, for example, methods of this aspect utilize a deep-depletion charge coupled device (CCD) detector or deep-depletion CMOS device for detecting particles. Deep-depletion CCD based detection methods are useful, for example, as two-dimensional detection of free electrons or holes generated by interactions between a particle and a depletion region optionally provide for techniques that determine a location of a particle in three dimensions as well as an absolute direction of travel of a particle.

For example, in a specific method embodiment of this aspect the step of detecting at least a portion of the particles from the source comprises the steps of: interacting each detected particle with a depletion region of a deep-depletion CCD device or deep-depletion CMOS device positioned to intersect at least a portion of the independent particle trajectory of each detected particle, where the interaction generates the first and second position dependent signals corresponding to free electrons or holes generated at the first and second points along the independent particle trajectory of each detected particle in the depletion region; and accelerating and accumulating the free electrons or holes in active CCD wells of the deep-depletion CCD detector or deep-depletion CMOS device. In an embodiment, a particle track detector comprises a deep-depletion CCD or deep-depletion CMOS device positioned proximate to the source of particles, wherein each particle track corresponds to a particle path within a deep-depletion region of the deep-depletion CCD device or deep-depletion CMOS device. In a specific embodiment, a step of recording an image of a particle track with a particle track detector comprises interacting a particle with a depletion region of a deep-depletion CCD detector or deep-depletion CMOS device positioned proximate to the source, wherein the interaction generates free electrons or holes along the particle track within the deep-depletion region of the deep-depletion CCD detector or deep-depletion CMOS device, wherein the generated free electrons or holes are accelerated toward and accumulated within a two-dimensional array of active CCD wells of the deep-depletion CCD detector or deep-depletion CMOS device.

In an embodiment, for example, diffusion of the free electrons or holes occurs as the free electrons or holes are accelerated toward the active CCD wells. For example, in an embodiment, an amount of diffusion is proportional to a depth in the depletion region. In an exemplary embodiment, an amount of diffusion causes a blur of the free electrons or holes accumulated in the active CCD wells, such that it permits independent detection and identification of the first and second position dependent signals or the position of a particle track within based on the blur amount.

Methods of the above described aspects are optionally useful for tomographic methods. For example, in embodiments, the above described methods for imaging a plurality of particles are used with tomographic techniques where a tissue sample is provided and sequentially sectioned to expose deeper and deeper layers within the tissue. As various embodiments are useful for determining the source of particles within an object, repeatedly detecting particles from the object using a particle detector that is positioned adjacent to subsequently deeper and deeper surfaces within the object can advantageously increase a sensitivity, detection and/or resolution at which the source of particles distributed throughout the object can be imaged. In embodiments, tomographic techniques incorporating the above described methods for imaging a plurality of particles are used to image an entire tissue sample, an entire organ or even an entire animal.

In embodiments, for example, tomographic methods useful with methods of the invention include microtomography, macrotomography, cryomicrotomography or cryomacrotomography. Tomographic methods of the invention are optionally useful, for example, when the source of particles is present within a tissue sample, such as a distribution of radiopharmaceuticals in a tissue or body. An exemplary embodiment of a method for imaging a source of particles further comprises a step of obtaining a white-light image of an exposed surface of the tissue sample. For example, in an embodiment, the white-light image is analyzed to obtain anatomical information or compositional information of the tissue sample.

In an embodiment, steps of detecting a plurality of particles and steps of obtaining a white-light image of an exposed surface of a tissue sample are repeated for a plurality of depths within the tissue sample in order to obtain white-light images of exposed surfaces of the plurality of depths within the tissue sample and to detect for each of the plurality of depths within the tissue sample a plurality of particles from the source. For example, in an embodiment, each white-light image comprises an image of an exposed surface of the tissue sample at a single depth within the tissue sample. In an embodiment, the plurality of depths are obtained by removing one or more layers of the tissue sample where removal of each layer of the tissue sample exposes a deeper surface of the tissue sample. In a specific method embodiment, the following steps are repeated for a plurality of depths within a tissue sample: repeating recording, determining and storing steps, thereby generating attributes for each of the plurality of depths, obtaining a white-light image of a surface of the tissue sample, thereby obtaining white-light images of exposed surfaces of the plurality of depths within the tissue sample and wherein the attributes comprises attributes of a plurality of particle tracks for each of the plurality of depths within the tissue sample. In an exemplary embodiment, the method further comprises a step of reconstructing a 3D distribution of the source of particles using the attributes of particle tracks for each of the plurality of depths within the tissue sample.

In an exemplary embodiment, a step of reconstructing a 3D image or distribution of a source of particles comprises reconstructing the 3D image or distribution of the source of particles using the plurality of depths of the tissue sample. For example, in an embodiment, the reconstructing step comprises reconstructing the 3D image or distribution of the source of particles using depth information for each of the plurality of depths of the tissue sample. In an embodiment, a step of reconstructing the 3D image or distribution comprises calculating probability density functions for each of a plurality of locations within the tissue sample. For example, in an embodiment, the probability density function for each location accounts for a depth at which the particle was detected. In an embodiment, for example, the probability density function for each location accounts for scattering of the particle along the independent particle trajectory between that location and the first or second points.

In an exemplary embodiment, scattering of the particle along the independent particle trajectory between that location and the first or second points is calculated from information obtained from the white-light images of exposed surfaces of a plurality of depths of the tissue sample. For example, in an embodiment, the information obtained from the white-light images of exposed surfaces of the plurality of depths of the tissue sample comprises one or more of anatomical information of the tissue sample, propagation properties for the anatomical information, tissue types present within the tissue sample and propagation properties for the tissue types. In an exemplary embodiment, the propagation properties are provided in a lookup table.

In an exemplary embodiment, a method for imaging a source of particles within a tissue sample comprises the steps of: obtaining a white-light image of an exposed surface of the tissue sample; detecting a plurality of the particles from the source by measuring first and second position dependent signals for each detected particle; where each detected particle traverses an independent particle trajectory; and where the first and second position dependent signals correspond to first and second points along the independent particle trajectory of each detected particle; repeating the obtaining step and the detecting steps for a plurality of depths within the tissue sample, where the plurality of depths are obtained by removing one or more layers of the tissue sample and where removal of each layer of the tissue sample exposes a deeper surface of the tissue sample, thereby obtaining white-light images of exposed surfaces of the plurality of depths within the tissue sample and detecting for each of the plurality of depths within the tissue sample a plurality of particles from the source; analyzing the white-light images of exposed surfaces of the plurality of depths within the tissue sample to determine anatomical or tissue type information of the tissue sample; analyzing the first and second position dependent signals for each detected particle to determine at least one position and at least one direction characterizing each independent particle trajectory; and reconstructing a 3D image of the source of particles using the positions and directions characterizing the independent particle trajectories of the detected particles, the plurality of depths within the tissue sample and the anatomical or tissue type information.

In an exemplary embodiment, a method for imaging a source of particles within a tissue comprises the steps of: obtaining a white-light image of an exposed surface of the tissue sample; repeating, for each of a plurality of particles from the source, the steps of a), b), and c): a) recording an image of a particle track with a particle track detector; b) determining attributes of the particle track using the particle track image; and c) storing the attributes of the particle track; with the method further comprising the steps of: repeating the obtaining step and the repeating of the recording, determining and storing steps for a plurality of depths within the tissue sample, wherein the plurality of depths are obtained by removing one or more layers of the tissue sample and wherein removal of each layer of the tissue sample exposes a deeper surface of the tissue sample, thereby obtaining white-light images of exposed surfaces of the plurality of depths within the tissue sample and generating particle track attributes for a plurality of particles from the source at a plurality of depths within the tissue sample; analyzing the white-light images of exposed surfaces of the plurality of depths within the tissue sample to determine anatomical or tissue type information of the tissue sample; and reconstructing a 3D distribution of the source of particles using the attributes for a plurality of particles from the source at a plurality of depths within the tissue sample, the plurality of depths within the tissue sample and the anatomical or tissue type information.

In an exemplary embodiment, a method for imaging a source of particles within a tissue sample comprises the steps of: recording images of a plurality of particle tracks with a particle track detector; determining attributes of the plurality of particle tracks from the images; storing the attributes of each of the plurality of particle tracks; repeating the detecting, determining and storing steps for a plurality of depths within the tissue sample, wherein the plurality of depths are obtained by removing one or more layers of the tissue sample and wherein removal of each layer of the tissue sample exposes a deeper surface of the tissue sample, thereby generating particle track attributes for a plurality of particles from the source at a plurality of depths within the tissue sample; and reconstructing a 3D image of the source of particles using the particle track attributes for a plurality of particles from the source at a plurality of depths within the tissue sample and the plurality of depths within the tissue sample.

In an exemplary embodiment, a method for imaging a source of particles within a tissue sample comprises the steps of: detecting a plurality of the particles from the source by measuring first and second position dependent signals for each detected particle; where each detected particle traverses an independent particle trajectory; and where the first and second position dependent signals correspond to first and second points along the independent particle trajectory of each detected particle; repeating the detecting step for a plurality of depths within the tissue sample, where the plurality of depths are obtained by removing one or more layers of the tissue sample and where removal of each layer of the tissue sample exposes a deeper surface of the tissue sample, thereby detecting for each of the plurality of depths within the tissue sample a plurality of particles from the source; analyzing the first and second position dependent signals for each detected particle to determine at least one position and at least one direction characterizing each independent particle trajectory; reconstructing a 3D image of the source of particles using the positions and directions characterizing the independent particle trajectories of the detected particles and the plurality of depths within the tissue sample.

In another aspect, the present invention provides devices for imaging a source of particles. An exemplary device embodiment comprises: an active material which generates detectable signals when each of a plurality of particles from the source interacts with the active material; a position sensitive detector for detecting first and second detectable signals generated as each particle traverses an independent particle trajectory in the active material, with the first and second detectable signals corresponding to first and second points along the independent particle trajectory of each detected particle, and where the position sensitive detector is positioned proximate to the active material, such as in optical communication with the active material; and a processor positioned in data communication with the position sensitive detector.

An exemplary device embodiment comprises an active material which generates detectable signals when each of a plurality of particles from the source interacts with the active material along a particle track; a position sensitive detector for detecting the detectable signals generated as each particle traverses an independent particle track in the active material, where the position sensitive detector is positioned proximate to the active material, such as at a position in optical communication with the active material; a processor positioned in data communication with the position sensitive detector, the processor programmed with instructions that when executed: analyze the detected detectable signals generated along each independent particle track to determine attributes of each independent particle track; and reconstruct a 3D image of the source of particles using attributes corresponding to all of the plurality of particles.

In an embodiment, a method of the invention further comprises, for each of the particles, storing the attributes of the particle track as entries in an attribute list, 4D grid of bins or a database. In an embodiment, the 3D distribution of the source of particles is reconstructed using the attribute list, 4D grid of bins or database. In a specific embodiment, the features and/or attributes of a particle track comprise at least one position and at least one direction characterizing each independent particle trajectory in the active material of a particle detector system. For example, in an embodiment, attributes of a particle track comprise one or more of a position of a start of a particle track, a direction of travel of a particle at a start of a particle track and a total energy deposited by a particle along particle track. For example, in an embodiment the features and/or attributes of a particle track comprise a 3D position and direction at a point at which a particle begins interacting with the active material. For example, in exemplary embodiments, the active material is positioned to intersect at least a portion of the independent particle trajectory of each detected particle. In an embodiment, for example, the active material comprises a scintillator, a microchannel plate, a depletion region of a deep-depletion CCD device or deep-depletion CMOS device. In an embodiment, for example, the position sensitive detector comprises a two-dimensional optical detector, a two-dimensional electronic detector, a CCD detector, a deep-depletion CCD detector, deep-depletion CMOS device, a CMOS detector, a MOS detector or an active pixel sensor.

Another device embodiment of this aspect comprises a position dependent detector for detecting a plurality of particles from the source by measuring first and second position dependent signals for each detected particle, with each detected particle traversing an independent particle trajectory and where the first and second position dependent signals correspond to first and second points along the independent particle trajectory of each detected particle; and a processor positioned in data communication with the position dependent detector. In an embodiment, for example, the track features and/or at least one position and/or at least one direction characterizing each independent particle trajectory comprises a 3D position and direction at a point of interacting with the position dependent detector. In an embodiment, for example, the direction at the point of interacting with the detector comprises two or more angles characterizing a direction of travel along the independent particle trajectory at the 3D position.

An exemplary device embodiment for imaging a source of particles comprises a particle track detector for recording images of detectable signals generated along particle tracks in an active material, wherein the detectable signals are generated by an interaction of a particle from the source with the active material; and a processor positioned in data communication with the particle track detector, wherein the processor is configured for: analyzing a plurality of images of detectable signals generated along particle tracks of a plurality of particles in an active material to determine attributes of the plurality particle tracks; and reconstructing a 3D image of the source of particles using attributes corresponding to all of the plurality of particles.

A variety of processors are useful with devices of this aspect. For example, general purpose processors for executing any instructions given to the processor can be optionally used. As another example, processors capable of executing only a limited instruction set are useful with devices of this aspect. In an embodiment, for example, processors used with embodiments of this aspect are programmed with instructions that when executed analyze the first and second signals for each particle to determine at least one position and at least one direction characterizing each independent particle trajectory; and reconstruct a 3D image of the source of particles using the positions and directions characterizing the independent particle trajectories of each detected particle. In an embodiment, for example, processors used with embodiments of this aspect are configured for: analyzing the first and second position dependent signals for each detected particle to determine at least one position and at least one direction characterizing each independent particle trajectory; and reconstructing a 3D image of the source of particles using the positions and directions characterizing the independent particle trajectories of the detected particles.

Another device embodiment for imaging a source of particles within a tissue comprises: a camera for obtaining a white-light image of a surface of the tissue; an active material which generates detectable signals when each of a plurality of particles from the source interacts with the active material; a position sensitive detector for detecting first and second detectable signals generated as each particle traverses an independent particle trajectory in the active material, wherein the first and second detectable signals correspond to first and second points along the independent particle trajectory of each detected particle, and where the position sensitive detector is positioned proximate to the active material, such as in optical communication with the active material; a mechanism for removing a layer from the tissue; and a processor positioned in data communication with the position sensitive detector and the camera, the processor programmed with instructions that when executed: analyze the first and second signals for each particle to determine at least one position and at least one direction characterizing each independent particle trajectory; analyze the white-light image of a surface of the tissue to determine anatomical or tissue type information of the tissue; and reconstruct a 3D image of the source of particles using the positions and directions characterizing the independent particle trajectories of each detected particle and the anatomical or tissue type information of the tissue. In an exemplary embodiment, a device of this aspect comprises a tomographic imaging system.

In an embodiment, a device for imaging a source of particles within a tissue comprises: a camera for obtaining a white-light image of a surface of the tissue; an active material which generates detectable signals when each of a plurality of particles from the source interacts with the active material; a position sensitive detector for detecting the detectable signals generated as each particle traverses an independent particle track in the active material, where the position sensitive detector is positioned proximate to the active material, such as in optical communication with the active material; a sectioning blade for removing a layer from the tissue; and a processor positioned in data communication with the position sensitive detector and the camera, the processor programmed with instructions that when executed: analyze the detected detectable signals generated along each independent particle track to determine attributes of each independent particle track; analyze the white-light image of a surface of the tissue to determine anatomical or tissue type information of the tissue; and reconstruct a 3D image of the source of particles using attributes corresponding to all or a portion of the plurality of particles and the anatomical or tissue type information of the tissue.

In a specific embodiment, the mechanism for removing the layer from the tissue comprises a sectioning blade or a milling type machining tool. In an embodiment, for example, a device of this aspect further comprises a positioning stage for adjusting a relative position between the tissue and the mechanism for removing a layer from the tissue. For example, in an embodiment, the positioning stage provides for removal of one or more layers of the tissue to expose surfaces of the tissue at a plurality of depths within the tissue. In an exemplary embodiment, the processor is programmed with instructions that when executed reconstruct the 3D image of the source of particles using the positions and directions characterizing the independent particle trajectories of each detected particle, the anatomical or tissue type information of the tissue and depth information corresponding to the plurality of depths within the tissue. In an embodiment, the processor is programmed with instructions that when executed: reconstruct the 3D image of the source of particles using attributes corresponding to all or a portion of the plurality of particles, the anatomical or tissue type information of the tissue and depth information corresponding to the plurality of depths within the tissue.

Methods and devices of the invention optionally are capable of detecting particles from a variety of sources. Useful particle sources are optionally located in either in vivo tissue or ex vivo tissue. For example, in one embodiment, the source of particles comprises a radiopharmaceutical administered to a patient, subject or tissue. In embodiments, methods of the invention comprise a step of administering a source of particles to a tissue or to a patient or subject, such as a radiopharmaceutical administered to a subject for distribution of the radiopharmaceutical in tissue of the subject. In an embodiment, for example, the 3D image of the source of particles comprises a distribution of the radiopharmaceutical in the tissue. In an embodiment, for example, methods and devices of the invention are useful for imaging a source of particles having a thickness of virtually any size, such as a thickness selected from the range of 1 µm to 10 mm or greater. Methods and devices of the invention are optionally useful, for example, for imaging a source of particles located at a surface of a tissue or at depth within a tissue selected from the range of 0 to 5 mm or from the range of 0 to 10 mm. In an exemplary embodiment, the source of particles comprises radioactive compositions within living tissue.

In exemplary embodiments, the devices and methods of the invention determine at least one position and at least one direction characterizing each independent particle trajectory, such as a 3D position and direction at a point at which a particle interacts with a detector for detecting particles, such as a particle track detector. In an embodiment, the at least one position and at least one direction are attributes of a particle track. In an embodiment, attributes of a particle track include one or more of a position of a start of the particle track, a direction of travel of a particle at a start of the particle track and a total energy deposited by a particle along a particle track. In a specific embodiment, a direction of travel of a particle at a start of the particle's track is characterized by two or more angles. In an embodiment, for example, the direction at the point of interacting with the detector comprises two or more angles characterizing a direction of travel along the independent particle trajectory at the 3D position. In an exemplary embodiment, the direction of travel is determined by approximating particle propagation processes taking place between the first and second points.

In embodiments, a step of analyzing the first and second position dependent signals for each detected particle to determine at least one position and at least one direction characterizing each independent particle trajectory comprises determining a direction of travel of each detected particle between the first and second points along the independent particle trajectory. In an embodiment, for example, the step of analyzing the first and second position dependent signals for each detected particle to determine at least one position and at least one direction characterizing each of the independent particle trajectories comprises determining a direction of travel of each detected particle at the first point along the independent particle trajectory or at the second point along the independent particle trajectory.

In embodiments, the devices and methods of the invention reconstruct a 3D image corresponding to a source of particles, such as a 3D tomogram of the tissue or a 3D distribution of the source of particles, such as a distribution of a radiopharmaceutical in a tissue. In embodiments, a step of reconstructing a 3D image comprises using a list-mode maximum-likelihood expectation-maximization algorithm to determine a 3D distribution of the source of particles. In embodiments, a step of reconstructing a 3D image comprises calculating for each detected particle a probability density function for each of a plurality of locations or voxels within the source of particles. In an embodiment, for example, the probability density function for each location is calculated using a Monte Carlo simulation. In exemplary embodiments, the probability density function for each location accounts for scattering of a particle along the independent particle trajectory or between that location and the particle detector. In an embodiment, the probability density function for each location accounts for scattering of a particle between that location and the first or second points.

In exemplary embodiments, a step of reconstructing the 3D image comprises determining a distribution of the source of particles within a tissue or sample to a specific precision or voxel size, such as 25 µm or less. In an embodiment, for example, a visual display of a 3D image or 3D distribution is provided by a device or method of the invention. In a specific embodiment, the 3D image comprises a spatial map illustrating a distribution of the source of particles within a tissue or sample.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 6a illustrates a pixel grid. FIG. 6b illustrates a region of interest of the grid of FIG. 6a. FIG. 6c depicts a schematic 2D-illustration of a reconstructed particle source.

DETAILED DESCRIPTION

Figure 1:
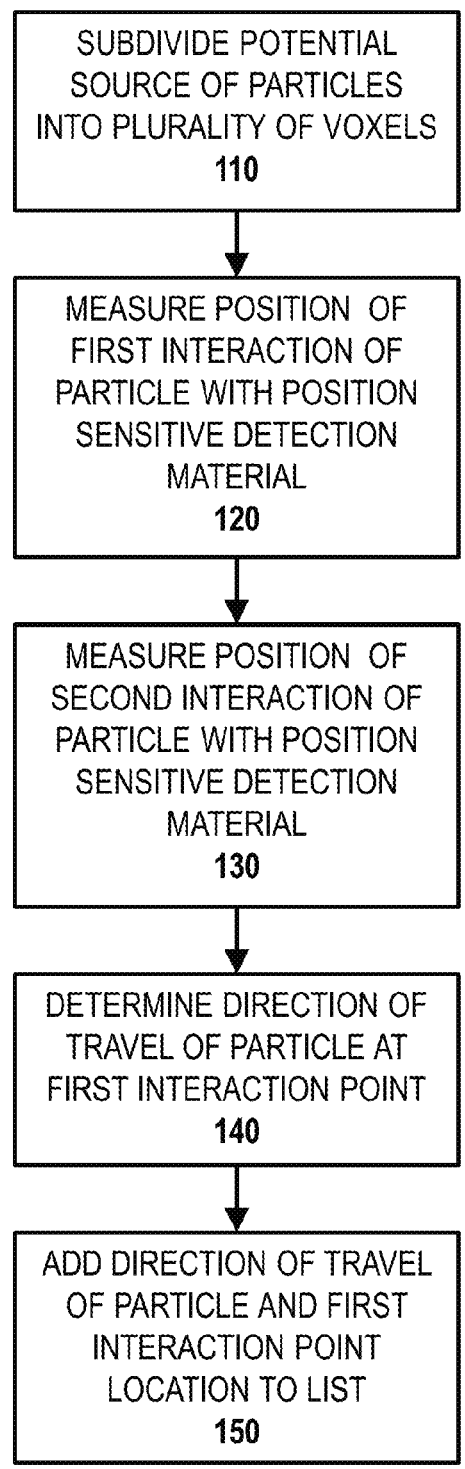
FIG. 1 provides an overview of a method for reconstructing the distribution of a source of particles within a tissue or object.

In general, the terms and phrases used herein have their art-recognized meaning, which can be found by reference to standard texts, journal references and contexts known to those skilled in the art. The following definitions are provided to clarify their specific use in the context of the invention.

"Particle" refers to an object possessing mass. Particles are distinguished from massless objects, such as photons. Exemplary particles include, but are not limited to, subatomic particles such as protons, neutrons and electrons, high energy particles such as alpha particles and beta particles, atomic nuclei, atoms and ions. As used herein, particles explicitly include alpha particles, beta particles, positrons, conversion electrons and auger electrons.

"3D position" refers to a unique location within space characterized by three coordinates, such as x, y, and z coordinates. In embodiments a 3D position can be provided by two coordinates (e.g., x and y) located within a plane or within a film or layer of material.

"Position dependent signal" refers to a signal generated by detection or measurement of a particle, such as a beta particle, alpha particle or a conversion electron, at a specific point on the trajectory of the particle. In some embodiments, position dependent signals are useful for characterizing the trajectories of particle translating from a source through a detection region. Position dependent signals include optical signals, electronic signals, acoustic signals, magnetic signals, and combinations of these.

"Interaction" refers to a process where a particle's kinetic energy is reduced when it is exposed to or otherwise interacts with a material, device or device layer to generate a detectable signal, such as electrons or photons.

"Active material" refers to a device, composition or structure that generates, upon an interaction with a particle, a detectable signal that originates from the specific location within the device, composition or structure that the interaction occurs at.

"Direction" refers to a description of the translation through space of a particle. In embodiments, the direction of travel of a particle is specified by two angles in a spherical coordinate system or by any two components of a unit vector.

"Scintillator," "scintillation material" and "phosphor" refers to a composition that emits photons upon an interaction with a particle, such as a beta particle, alpha particle or conversion electron. In embodiments, photons are emitted by these materials upon absorption of a particle. In embodiments, photons are emitted by these materials when these materials interact with a particle and reduce the particle's kinetic energy.

"CCD" refers to or "charge-coupled device" refers to an imaging device used for detection of electromagnetic radiation by generation of and or accumulation of charges upon absorption of electromagnetic radiation. In embodiments, the term CCD refers to a two-dimensional array of CCD elements arranged to obtain an image.

"Deep-depletion CCD" refers to a specific CCD construction where the semiconductor material comprising the active charge generation region or depletion region is thicker than in a conventional CCD device such that it permits detection of absorbed radiation or particles at depths greater than conventional a CCD. "Depletion region" refers to a region of a CCD in which there is a high electric field for the purpose of separating electrons and holes. "CCD well" refers to a region of a CCD or deep-depletion CCD in which charges generated through the absorption of electromagnetic are accumulated.

"CMOS sensor" refers to an imaging device used for detection of electromagnetic radiation. In embodiments, a CMOS sensor is fabricated using conventional methods and technology commonly known in the art of microfabrication and integrated circuit fabrication as "complementary metal-oxide-semiconductor."

"White-light image" refers to an image created or displayed using a two dimensional optical detector, such as an image sensor including, but not limited to, a digital camera, a charge-coupled device (CCD) detector, a complementary metal-oxide-semiconductor (CMOS) detector, or a metal-oxide-semiconductor (MOS) detector. In some embodiments, a white-light image is generated by illuminating a sample using an optical source providing electromagnetic radiation characterized by a plurality of wavelengths, and detecting light scattered, reflected and/or emitted by the sample. In an embodiment, for example, a white light image is generated by illumination with a broad band electromagnetic source providing electromagnetic radiation having wavelengths in the visible and/or infrared regions.

"Semiconductor" refers to any material that is an insulator at very low temperatures, but which has an appreciable electrical conductivity at temperatures of about 300 Kelvin. In the present description, use of the term semiconductor is intended to be consistent with use of this term in the art of microelectronics and electrical devices. Typical semiconductors include element semiconductors, such as silicon or germanium, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as AlxGa1-xAs, group II-VI semiconductors such as CsSe, CdS, CdTe, ZnO, ZnSe, ZnS, and ZnTe, group 1-VII semiconductors CuCl, group IV-VI semiconductors such as PbS, PbTe and SnS, layer-type semiconductors such as $Pbl_2$, $MoS_2$ and GaSe, oxide semiconductors such as CuO, $Cu_2O$ and $TiO_2$. The term semiconductor includes intrinsic semiconductors and extrinsic semiconductors that are doped with one or more selected materials, including semiconductor having p-type doping materials (also known as p-type or p-doped semiconductor) and n-type doping materials (also known as p-type or n-doped semiconductor), to provide beneficial electrical properties useful for a given application or device. The term semiconductor includes composite materials comprising a mixture of semiconductors and/or dopants. Impurities of semiconductor materials are atoms, elements, ions and/or molecules other than the semiconductor material(s) themselves or any dopants provided to the semiconductor material. In embodiments, an interaction between a semiconductor and a particle, such as a beta particle, alpha particle, or conversion electron, generates electron-hole pairs within the semiconductor. In embodiments, an interaction between a semiconductor and a particle, such as a beta particle, alpha particle or conversion electron, generates electron-hole pairs which are separated within the depletion region of a semiconductor device.

"Resistive anode encoder" refers to a position sensitive detector used for detecting the spatial position of charged or energetic particles, such as electrons. In embodiments, a resistive anode encoder is used in conjunction with an electron multiplying structure, such as a microchannel plate, and employs a resistive element for collection of multiplied charge generated upon absorption of or interaction of the electron multiplying structure with a charged or energetic particle.

"Microchannel plate" or "MCP" refers to an electron multiplying structure used for the detection of charged or energetic particles, such as electrons and photons. In embodiments, a microchannel plate comprises a two-dimensional array of microchannels and is used for amplifying incident light or electric charge. In embodiments, a microchannel plate is coupled to a light generating material, such as a phosphor screen, to generate a detectable optical signal.

In embodiments, a detectable signal generated by a microchannel plate and phosphor screen pair is imaged using a camera or other imaging detector and provides for determining a spatial location of the incident charged or energetic particle.

"Radiopharmaceutical" refers to a radioactive composition administered to a subject or patient for use in the diagnosis, treatment, cure or prevention of a disease or condition or for use in imaging a tissue or tissue component. In embodiments, a radiopharmaceutical comprises one or more radioisotopes which generate particles upon radioactive decay, such as beta particles and/or alpha particles. In some embodiments, radiopharmaceuticals generate gamma rays.

"Detectable signal" refers to charged particles, such as electrons, or electromagnetic radiation that can be used for sensing the occurrence of an interaction between a particle and an active material of a position sensitive detector system.

"List-mode maximum-likelihood expectation-maximization algorithm" or "LMMLEM algorithm" refers to method for image reconstruction. An embodiment of this algorithm is described in L. Parra and H. H. Barrett, "List-mode likelihood—EM algorithm and noise estimation demonstrated on 2D-PET," IEEE Trans. Med. Imag. MI-17:228-235, 1998, which is hereby incorporated by reference.

"Monte Carlo simulation" or "Monte Carlo method" refers to a computational algorithm for determining a probability distribution or likelihood of the occurrence of an event. In embodiments a Monte Carlo simulation of an event is computed using a commercial software package or a publically available software package.

"Particle track" refers to the path of a particle through an active material, such as a scintillator or a microchannel plate or depletion region of a deep-depletion CCD device or deep-depletion CMOS device, along which a detectable signal is generated. A particle track generally begins at the point at which the particle enters the active material. In an embodiment, the particle track optionally ends when the particle exits the material. In an embodiment, the particle track optionally ends when the particle comes to a stop. A "particle track detector" refers to a system for capturing a detectable signal generated as a particle traverses a path through an active material.

FIG. 1 provides an overview of a method embodiment for determining or reconstructing the distribution of a source of particles within a tissue or object. Initially, (110) the particle source is subdivided into a plurality of volumetric pixels (voxels). The size of the voxels affects the resolution of the reconstruction achieved by the methods of the invention. Next, (120) for a single particle generated within the sample of interest, the particle is first interacted with a position sensitive detection material, such as a scintillator, and the position of this interaction is determined. Next, (130) the position of a second interaction between the particle and a position sensitive detection material is determined. In embodiments, the two positions are locations in physically separate position sensitive detection materials, such as two separate phosphor foils. However, other embodiments employ a thick position sensitive detection material, such as a thick scintillation material, in which a track of interactions with the particle are generated and the two positions are locations within this track, such as a starting point and another point along the track, or multiple, points along the track. From these positions, the direction of travel of the particle at the first interaction point is determined (140). Optionally, the direction of travel is represented as one or more angles. Once the direction of travel of the particle at the first interaction point is determined, this information is added to a list, 4D grid or other database for later reconstruction of the distribution of source of the particle (150).

Figure 2:
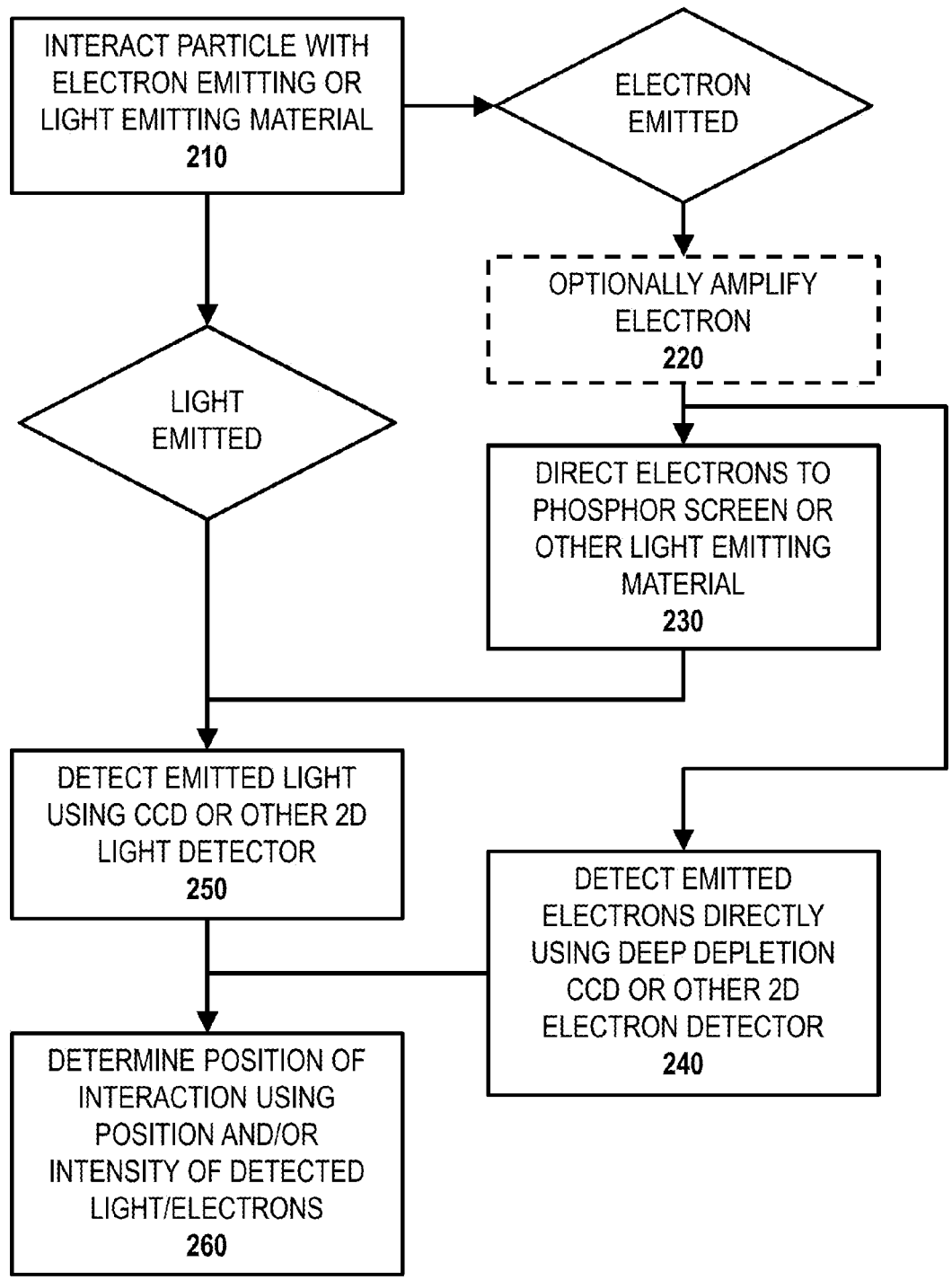
FIG. 2 provides an overview of a method for detecting an interaction of a particle with a light-emitting or electron emitting material.

FIG. 2 provides an overview of a method embodiment for detecting an interaction of a particle with an active material of a detector, such as a light-emitting or electron-emitting material. In this embodiment, the interaction generates a detectable signal. For example, the active material optionally comprises an electron emitting material or optionally comprises a light-emitting material and the particle is interacted with this material (210). Useful light-emitting materials include scintillators and phosphors. Useful electron emitting materials include photocathodes, semiconductor materials and microchannel plates. If the interaction with the particle generates an electron, the electron is optionally amplified (220), such as occurs in photomultiplier and microchannel plate systems, for subsequent detection. The electron or amplified electrons can be directed to a phosphor screen (230) or detected directly, such as by a deep depletion CCD system (240). If the interaction between the particle and the position sensitive detection material emits light or if the emitted electron is directed to a phosphor screen which then emits light, the emitted light is detected, for example, using a CCD (250). In either case, the position of the interaction is then determined using the position and/or intensity of the detected light or electrons (260).

Figure 3:
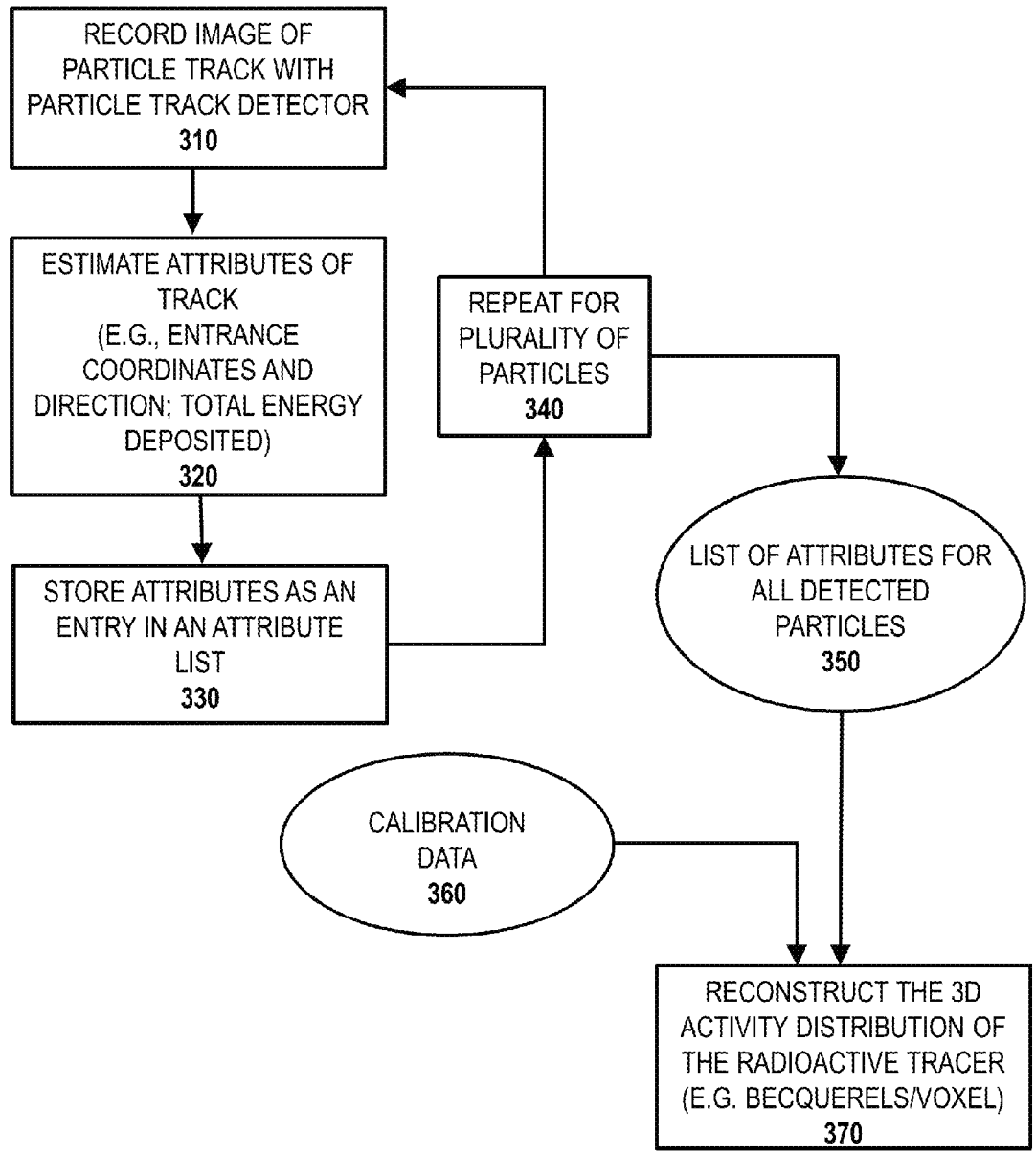
FIG. 3 provides an overview of a method for reconstructing the activity distribution of a particle source within a tissue, such as a radioactive tracer.

FIG. 3 provides an overview of a method for reconstructing the activity distribution of a particle source within a tissue, such as a radioactive tracer. First, an image of a particle track is recorded using a particle track detector (310). Next, attributes or features of the particle track are determined, such as entrance coordinates and direction, total energy deposited within the track, etc. (320). The attributes or features of the particle track are stored as entries in a list (330). The above steps are repeated for a plurality of particles (340) to generate a plurality of entries in the list, with each list entry corresponding to the attributes or features of a single particle track. Using the list of attributes for all detected particles (350) and, optionally, additional calibration data (360) the 3D activity distribution of the radioactive tracer is reconstructed (370). The invention also can be carried out via methods using other database approaches, such as by populating the attributes in a 4D grid or other database representation.

Figure 4:
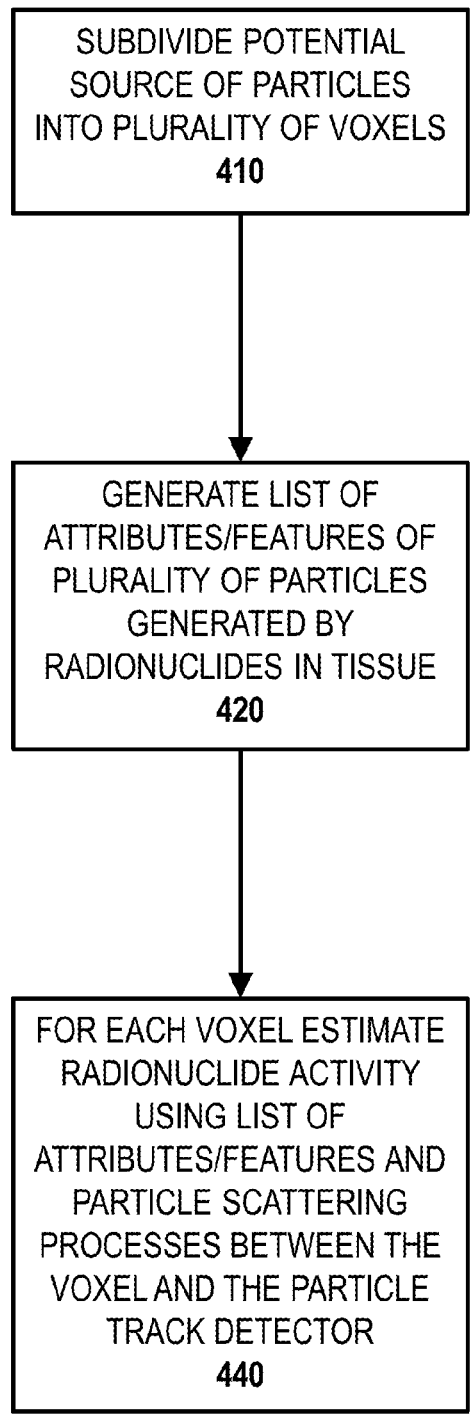
FIG. 4 provides an overview of a method for determining the particle emitting activity of radionuclides in a tissue.

FIG. 4 provides an overview of a specific method embodiment for reconstructing the particle emitting activity of radionuclides in a tissue. Here, the source of particles is subdivided into a plurality of voxels (410). A list of attributes/features of a plurality of tracks in a particle track detector generated by interaction of the particle track detector with a plurality of particles from the radionuclides in the tissue is provided, determined or otherwise generated (420), such as by the methods described herein employing track detectors to determine features/attributes of particle tracks. The list of attributes/features and estimated or simulated particle propagation processes in the tissue/material between each voxel and the particle track detector are then used to reconstruct the activity of the radionuclides at each voxel (430).

Figure 5:
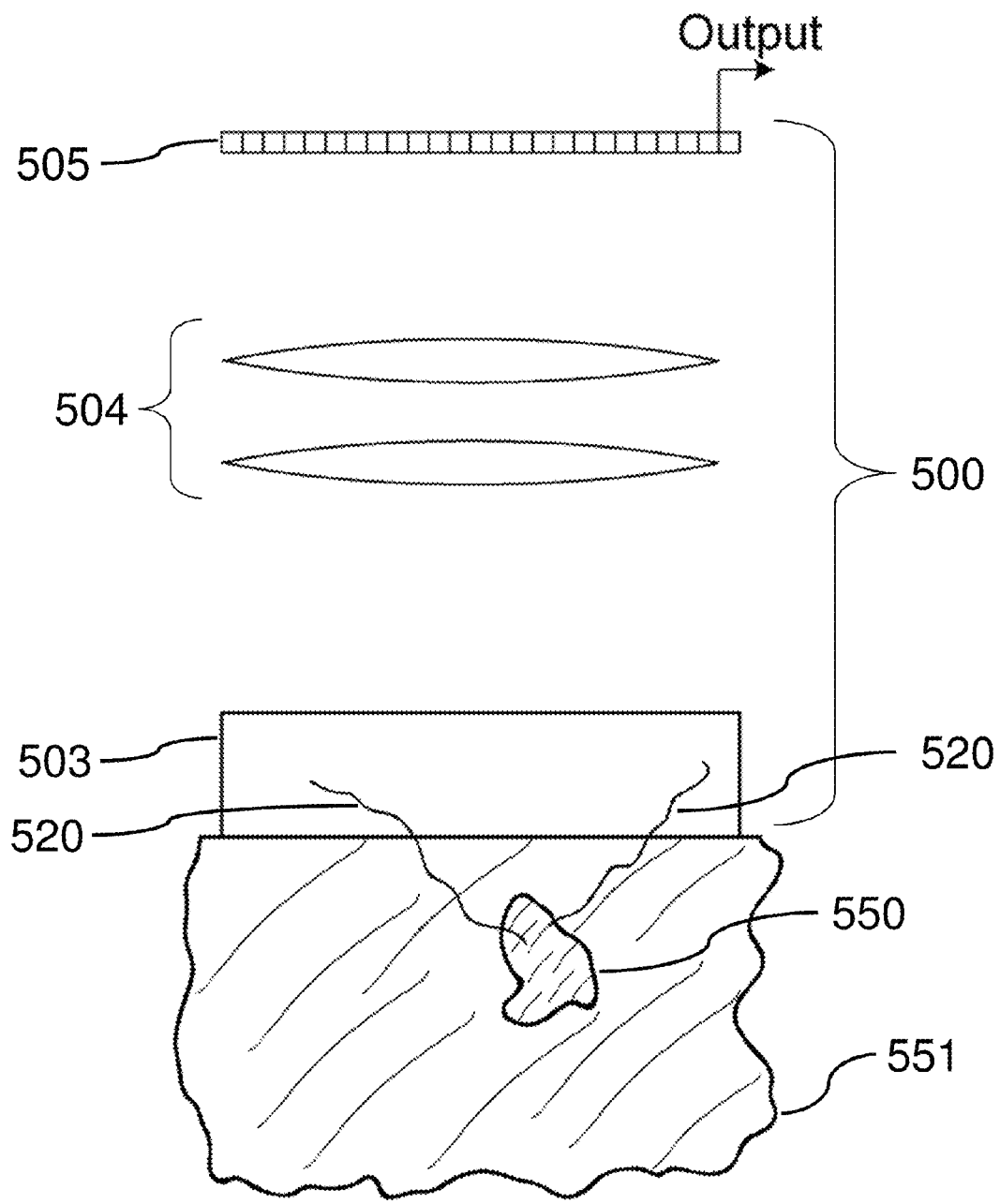
FIG. 5 depicts a system for observing electron tracks.

FIG. 5 illustrates an exemplary embodiment of a system 500 for determining a 3D representation of a particle-generating object 550 located within a tissue 551. System 500 comprises a thick scintillator 503, imaging lenses 504 and CCD 505. Particles generated by particle-generating object travel along paths 520 through tissue 551, where they optionally undergo absorption and scattering. When the particles reach scintillator 503, interactions along paths 520 between the particles and scintillator 503 generate electromagnetic radiation which is collected by lenses 504 for subsequent detection by CCD 505. The particles also optionally undergo absorption and scattering as they travel through scintillator 503. In embodiments, particles generate electromagnetic radiation along their entire track through scintillator 503. A processor (not shown) receives the output from CCD 505 for subsequent analysis of the detected electromagnetic radiation images.

FIG. 6*a* illustrates a pixel grid overlaid on particle generating object 550 and tissue 551. Although the depiction provided in FIG. 6*a* illustrates a 2-dimensional array of pixels, embodiments of the invention utilize a 3-dimensional pixel array or voxel grid. FIG. 6*b* narrows the pixel grid to a region of interest including the particle generating object. After a plurality of particles are interacted with a system for measuring particle tracks, such as described herein, the interaction points and directions of travel for the particles can be used to reconstruct an image of the particle generating object, here represented as an activity distribution. FIG. 6*c* depicts a schematic illustration of a reconstruction of particle generating object 550 for the narrowed pixel grid of FIG. 6*b* as an intensity map, where the shade of the pixel represents the activity of the particle emitting object within that pixel (white=low activity, black=high activity).

The invention may be further understood by the following non-limiting examples.

Example 1: Autoradiography Methods

Autoradiography is the use of a radioactive pharmaceutical to study clinical or biological processes. The radiation source is inside the object being studied, and the prefix 'auto' distinguishes it from conventional radiography where an external radiation source is used. Sometimes SPECT (single-photon emission computed tomography) and PET (positron emission tomography), which also use internal radioactive sources, are referred to as in vivo autoradiography, but the term is used much more commonly to refer to ex vivo imaging of a tissue specimen after a biopsy of a patient of in an animal imaging study after the animal is sacrificed.

In these procedures, the radiopharmaceutical is introduced into the living subject, and after a suitable time for it to equilibrate, the specimen is removed and cut with a device called a microtome into very thin slices, often only 5-10 μm thick. Each slice is then placed over a high-resolution imaging detector which is sensitive to charged particles, such as alpha particle, beta particles or Auger electrons, that are emitted by the radioactive isotope used in the pharmaceutical. Depending on the isotope, there may also be x-ray or gamma ray emissions, which can be used for in vivo tomography, but the imaging detectors used in ex vivo autoradiography are designed to be relatively insensitive to these photon emissions.

The resulting 2D autoradiographic slice images can have exquisite spatial resolution, far better than that of SPECT or PET; they can display the details of the radiopharmaceutical distribution at a cellular or subcellular level, but of course only after the specimen is no longer part of a living subject. In principle the 2D slice images can also be assembled into a 3D image, analogous to those produced by SPECT and PET, but in practice this procedure is both laborious and technically challenging. The technical challenges stem from distortions introduced by the transfer of tissue from the microtome and the imaging detector and/or the tissue dehydration process.

One goal achieved by the present invention is extension of 2D autoradiography to 3D, such that the full volumetric distribution of the pharmaceutical is imaged without having to reassemble the 3D volume from distorted 2D slices.

A second goal achieved by the present invention is performing the 3D imaging on a thick slab of tissue, rather than using thin slices at all.

A third goal achieved by the present invention is obtaining the 3D image with a detector in contact or near contact with just one face of the thick slab of tissue being imaged, rather than surrounding the tissue with detectors as in SPECT or PET.

A further goal is achieved by the present invention is achieving the first three goals with very high spatial resolution, much better than in SPECT or PET, rivaling that of thin-slice autoradiography.

These goals give 3D autoradiography uses for in vivo imaging, not just ex vivo.

An aspect of one embodiment of the invention is the use of charged-particle detectors that provide information about not only the location of the particle when it interacts with the detector but also its direction. With photon detectors, as in SPECT and PET, there is no possibility of learning anything about the direction of the photon from a single interaction with the detector. A high-energy photon travels unimpeded through a detector until it makes a Compton or photoelectric interaction at a single point; in a scintillation detector, each interaction produces a single flash of light. A high-energy charged particle, on the other hand, interacts with the detector all along its path. In a scintillation detector, light is produced at every point, and the whole track of individual particles can be recorded in a fast CCD or CMOS camera.

In a preferred embodiment, one face of a transparent scintillator is placed in contact or near contact with a thick piece of tissue, either excised or still part of the living subject. Radioactive decays of the pharmaceutical in the tissue produce charged particles that can escape from the tissue and enter into the scintillator. The light produced as the particle traverses its track in the scintillator can then be imaged by a lens or fiber-optics assembly coupled to the opposite face of the scintillator. If the camera is fast enough and sensitive enough, it can image the entire tracks produced in the scintillator by individual charged particles.

As discussed below, this example describes algorithms to determine the position and direction of the track at the point it enters the scintillator. This information is stored about each particle, for example, in a list, 4D grid or other database, and it is used, along with a sophisticated particle transport algorithm, to reconstruct the 3D distribution of the radioactive pharmaceutical.

Major advantages achieved by the embodiments described herein include the ability to produce high-resolution 3D imaging of the distribution of a radioactive pharmaceutical in a thick piece of tissue without physically slicing it into thin sections. In addition, this technique is applicable to virtually any radioisotope.

3D tomography with a detector on only one side of the tissue can be achieved by the techniques described herein. In addition, the techniques described herein are applicable to living tissue, for example with skin lesions or epithelial lesions accessible with endoscopy. Furthermore, dynamic (4D) studies on living subjects can be achieved.

Optionally, the slab of tissue being imaged must be thin enough that a significant fraction of the charged particles produced can escape from the slab and enter the charged particle track detector. For the energies of typical beta particles used in autoradiography, this limits the maximum of the tissue thickness for some embodiments to 2-10 mm.

Even if enough particles escape, they undergo significant scattering and absorption in the tissue, so the spatial resolution will degrade with the depth of the radioactive emission in the tissue.

Example 2: Charged-Particle Track Detectors

This example describes using electron tracks in a detector to measure the direction as well as the position of individual electrons emerging from tissue. Several types of detector are optionally used for such detection, including CCD-based systems that use multiple thin scintillator foils; bare microchannel plates (no scintillator or photocathode) that can be excited by direct electron interaction, and CCD detectors with thick depletion regions, again excited by direct electron interaction.

Figure 7:
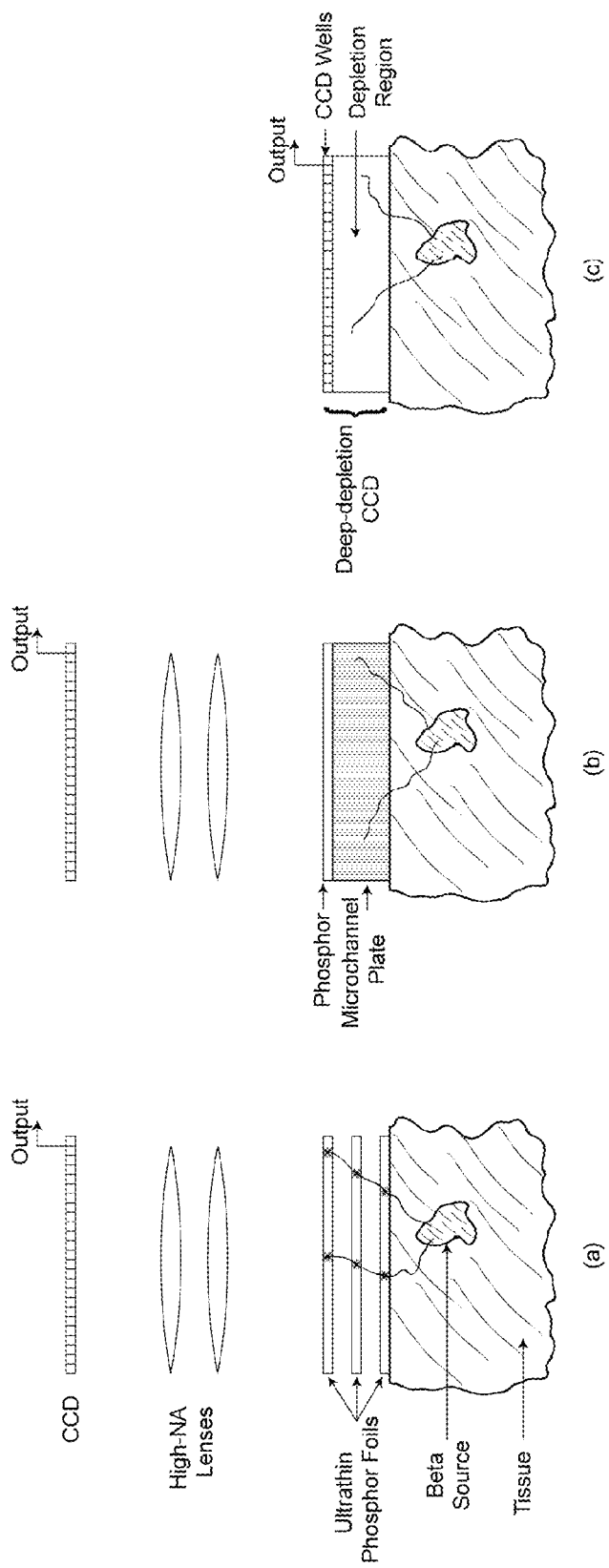
FIG. 7 (panels a-c) provides an overview of variety of detector embodiments for observing electron tracks.

The use of multiple thin foils is illustrated in FIG. 7 (panel a). The high-NA lens pair is optionally focused on the lower foil, and the other two foils will be slightly out of focus, allowing for identifying which foil a particular spot of light is produced from. Optionally, this geometry uses foils that do not scatter light from lower foils. Optionally, thin films of ZnO with various dopants such as Er, Ga and In are utilized. In one embodiment, a foil is formed using RF sputtering of ZnO. Other options include single-crystal films of YAG:Ce, LAG:Eu or GGG:Eu, optionally grown by liquid-phase epitaxy.

The bare microchannel plate is shown in FIG. 7 (panel b). In this case, either the specimen being imaged is in a vacuum chamber or there is an electron permeable entrance window, such as a very thin glass or metal entrance window. A high-energy electron passes through the window (if present) and then through multiple channels, exciting secondary electrons into the vacuum in each. These electrons are multiplied with a gain that depends strongly on where along the channel the secondary is produced, so relative intensities optionally provide information on the depth of interaction, providing observation of a 3D profile of the track.

The CCD with a thick depletion region is shown in FIG. 7 (panel c). Here the electron track is produced in the silicon depletion region, where a high electric field exists, and the secondaries along the track are accelerated (without gain) towards the active CCD well. Diffusion causes greater blur for longer translation paths, so again depth of interaction can be discerned. Thick-depletion device can also be CMOS, as in the WidePix device.

The angular information acquired is optionally used in planar imaging or in BET (Beta Emission Tomography). Listmode EM reconstruction likelihoods are optionally based on the observation that the estimates of direction and position are asymptotically normal. The resulting tomographic images are optionally displayed conventionally or summed in the z direction (normal to the detector), to get a 2D projection of the 3D distribution; in either case comparison images can, for example, be recorded by imaging the planar beta sources in direct contact with a thin-foil scintillator, such as without intervening plastic.

Optionally, image data is acquired with thick tissue slices, such as from an animal study. The thick slices are optionally cut into 10 μm slabs to be imaged with standard autoradiography, to permit the reconstructed images to be compared to the autoradiographs.

Figure 8:
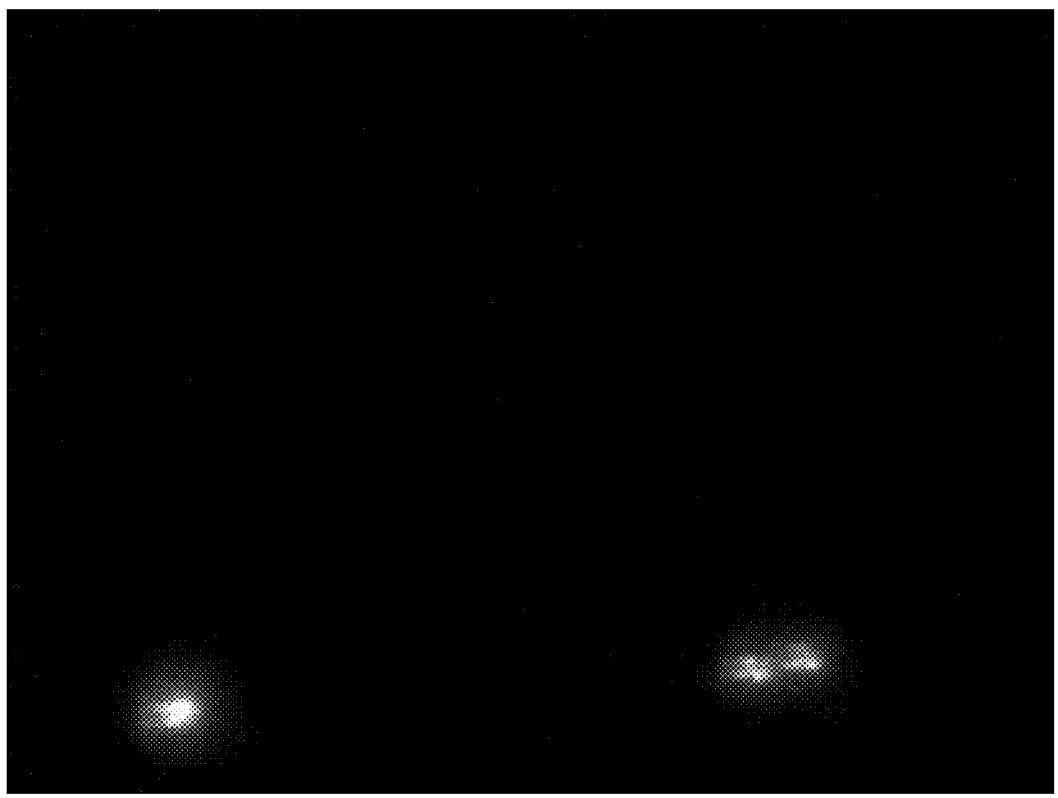
FIG. 8 provides a sample image from a charged particle track detector.

Track detector data with the setup depicted in FIG. 7 (panel b) was obtained. A sample image is shown in FIG. 8. The radionuclide activity and the camera frame rate were such that only one beta particle contributed to the image, but it interacted with the image intensifier in three places. A line drawn through the three points defines the beta track, which is about 1 mm long.

Alternative detectors. In some embodiments, an alternative to the track detectors shown in FIG. 7 (panels a-c) are employed. In one embodiment, a detector, referred to as BazookaSPECT when it is used with gamma rays, is utilized. It is described in detail in references provided below.

REFERENCES

Miller, Brian W. 2011. Dissertation. High-Resolution Gamma-Ray Imaging with Columnar Scintillators and CCD/CMOS Sensors, and FastSPECT III: A Third-Generation Stationary SPECT Imager.

B. W. Miller, H. H. Barrett, L. R. Furenlid, H. B. Barber, and R. J. Hunter, "Recent advances in BazookaSPECT: Real-time data acquisition and the development of a gamma-ray microscope," *Nucl. Inst. Meth.* A, 591(1):272-275, 2008. PMCID: PMC2597870.

B. W. Miller, L. R. Furenlid, S. K. Moore, H. B. Barber, V. V. Nagarkar and H. H. Barrett, "System integration of FastSPECT III, a dedicated SPECT rodent-brain imager based on BazookaSPECT detector technology," *IEEE Nucl. Sci. Symp. Conf. Record*, 4004-4008, 2009.

B. W. Miller, H. B. Barber, L. R. Furenlid, S. K. Moore and H. H. Barrett, "Progress in BazookaSPECT," *Proc. SPIE*, 7450:7450C, 2009. PMCID: PMC3033223

B. W. Miller, H. B. Barber, H. H. Barrett, Z. Liu, V. V. Nagarkar and L. R. Furenlid, "Progress in BazookaSPECT: high-resolution dynamic scintigraphy with large-area imagers," *Proc. SPIE* 8508:85080F, 2012.

B. W. Miller, H. H. Barrett, H. B. Barber and D. W. Wilson, "Gamma-ray microscopy using micro-coded apertures and Bazooka SPECT, a low-cost, high-resolution image intensifying gamma camera," 334366:158, Annual Meeting of the Society of Nuclear Medicine, Washington, D.C., Jun. 2-6, 2007.

B. W. Miller, D. R. Fisher, L. R. Furenlid, B. M. Sandmaier, J. M. Pagel, A. Kenoyer, S. Frost, D. S. Wilbur, D. Hamlin, E. Santos, O. Press, "Digital autoradiography with the iQID alpha camera", Targeted Alpha Therapies Conference (submitted)

U.S. Pat. No. 7,928,397 (Apr. 19, 2011) B. W. Miller, H. H. Barrett, H. B. Barber and L. R. Furenlid, "Gamma camera including a scintillator and an image intensifier."

H. H. Barrett, H. B. Barber, L. R. Furenlid and B. W. Miller, "An X-ray/CT photon-counting detector," U.S. Patent Application submitted (continuation in part of U.S. Pat. No. 7,928,397)

Figure 9:
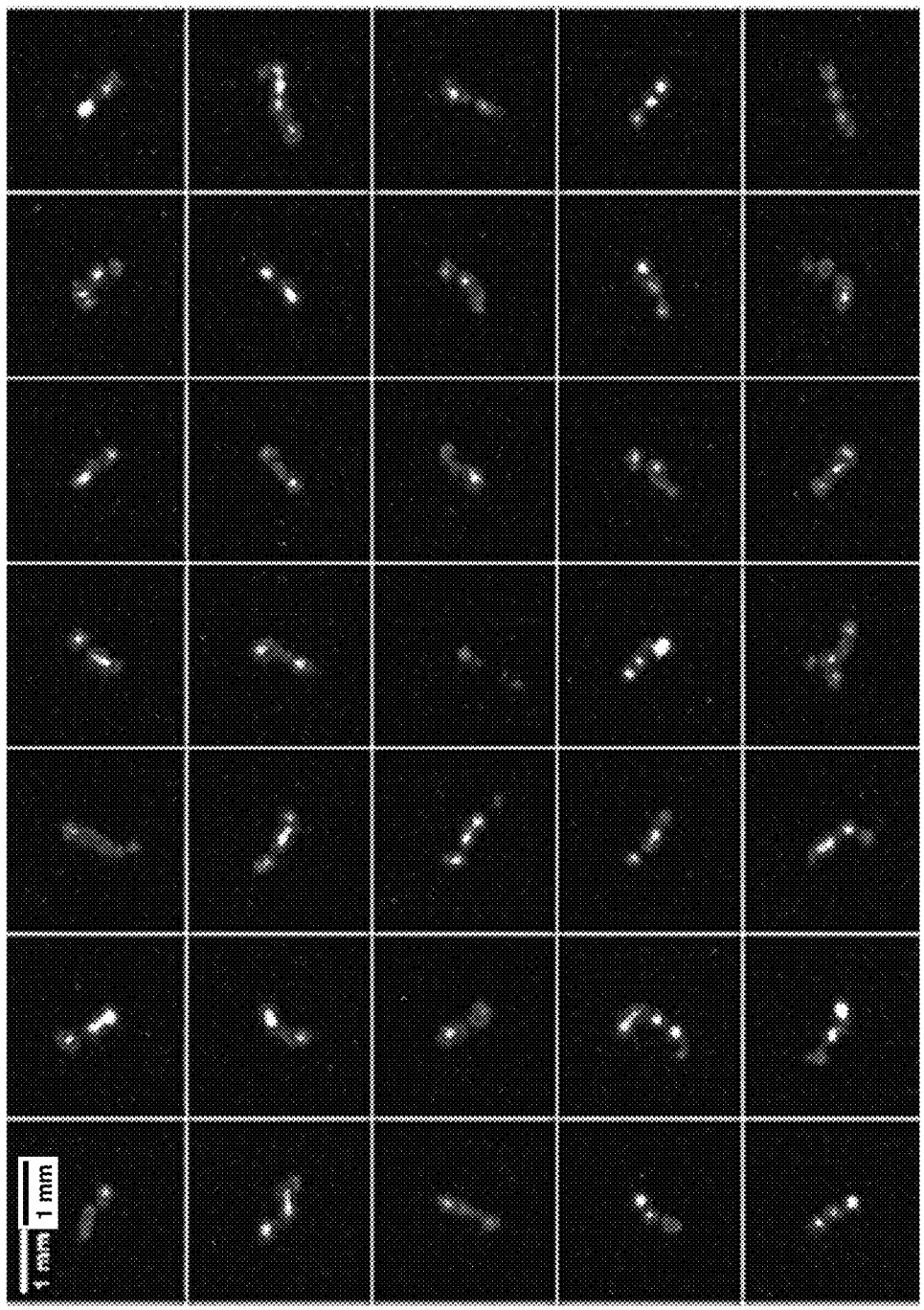
FIG. 9 depicts a collection of iQID beta particle track images.

In an embodiment, a BazookaSPECT type detector is converted to a track detector by using a thick, transparent scintillation material. For example, in one embodiment, this was achieved by using a 1-2 mm thick plastic scintillator, or an x-ray fluorescent screen. The resulting charged-particle detector is optionally referred to herein as iQID (ionizing-radiation Quantum Imaging Detector). A collection of iQID beta particle track images are shown in FIG. 9.

From Tracks to 3D Reconstructions.

As noted above, one desirable piece of information about each of the beta particles is the point at which it emerges from the tissue and enters the detector and its direction of travel at this point. The entrance point is specified by two coordinates (x, y) and direction by two angles (θ, φ). The description above discusses how this information can be obtained for each of the configurations shown in FIG. 1. In embodiments, a difficulty is encountered for extraction of this information from the iQID tracks described above because of the ambiguity as to which end of the track is the beginning and which the end.

A preferred embodiment for image reconstruction is the list-mode maximum-likelihood expectation-maximization algorithm (LMMLEM) algorithm described in L. Parra and H. H. Barrett, "List-mode likelihood—EM algorithm and noise estimation demonstrated on 2D-PET," IEEE Trans. Med. Imag., MI-17:228-235, 1998.

In this embodiment, the data set for this algorithm is a list of the coordinates and angles for each of the detected tracks. Formally, the data list is denoted as G={$x_j$, $y_j$, $θ_j$, $φ_j$; j=1, . . . J}, where the curly brackets denote a set, index i specifies a particular track, and J is the total number of tracks in the data set. The LMMLEM algorithm iteratively seeks a non-negative representation of the radionuclide distribution, denoted f, which maximizes the likelihood, defined as the probability density function (PDF) of the observed data, conditional on the radionuclide distribution; this likelihood is denoted as pr(G|f).

The likelihood is determined by the beta particle propagation processes in the tissue that contains the unknown radionuclide distribution f. If f is represented on a finely sampled voxel grid, the likelihood calculation boils down to computing the PDF of ($x_j$, $y_j$, $θ_j$, $φ_j$) given that a beta particle was emitted from a particular voxel, denoted by index n. A good approximation to this PDF is optionally obtained from standard Monte Carlo simulation programs such as GEANT4. The calculation can optionally assume that the tissue propagation properties are independent of position, which is often a valid model for soft tissue.

Figure 10:
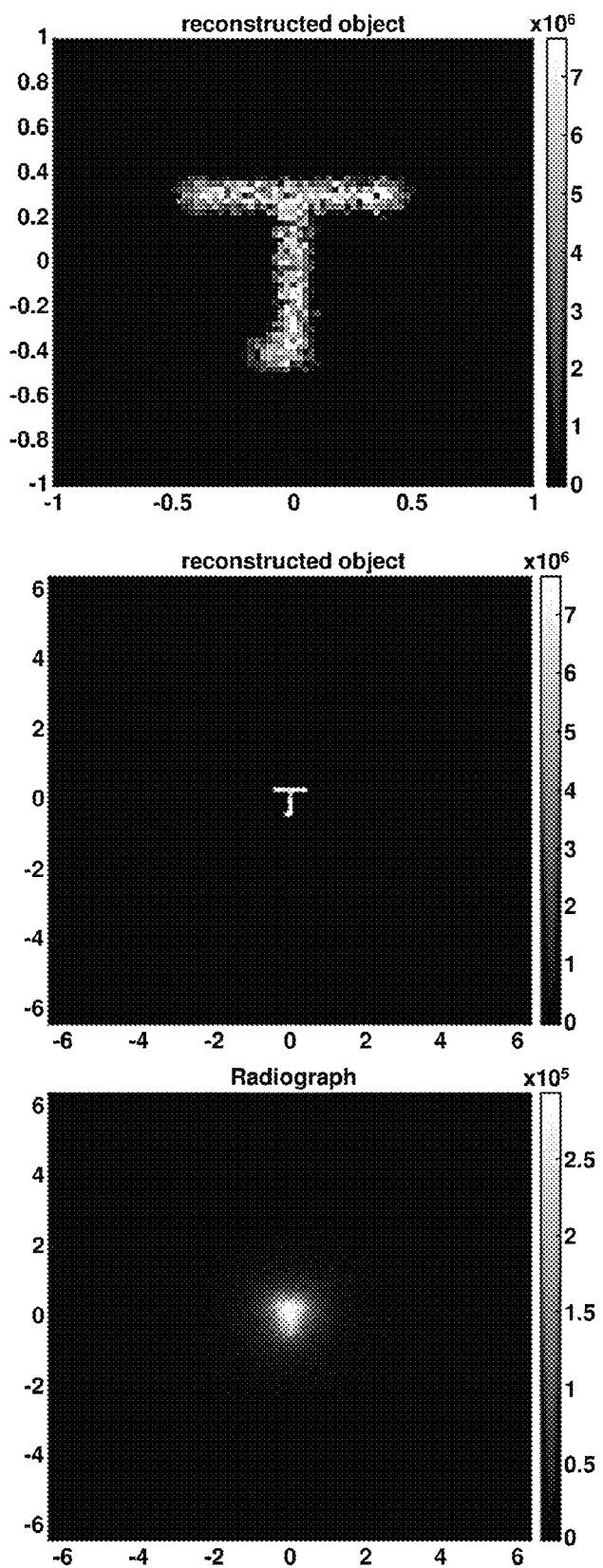
FIG. 10 provides simulated reconstruction results.

The results of a simulation study are shown in FIG. 10. The tissue was modeled as a uniform water-equivalent slab of thickness 10 mm, and the radionuclide distribution was confined to a box of thickness 0.1 mm, with the center of the box 0.4 mm below the surface, on which the emerging positions and directions of the betas were measured. The electron range was about 5 mm.

The image on bottom shows a simulated conventional autoradiograph, with the image highly blurred by the 0.4 mm of scattering material between the planar object and the tissue exit face. The center image shows the reconstructed object (the Chinese character ding) on a 10 mm×10 mm field of view, and the top image is a reconstruction of the same object on a 1 mm×1 mm field of view. The voxel size is 25 μm.

Issues with Track Detectors.

The simulated reconstructions above were obtained from a data list that accurately specified the position and direction of each detected beta particle at the point where it emerged from the tissue. With the iQID tracks, a fairly accurate determination of the locations of both ends of the track can be made, and the slope of the track at each end gives the corresponding particle directions, but there remains the problem of not knowing which end is which.

A straightforward modification of the LMMLEM algorithm optionally resolves this ambiguity. The basic idea is to store the positions and directions of the particle at both ends of the iQID track for each event and to treat the knowledge of which end is the beginning of the track as a hidden variable. It is then possible to derive a modified EM algorithm that simultaneously maximizes the probability of the data list given the object f and the labels specifying the beginning point of each track.

Another issue with any of the track detectors is the necessity of resolving an individual track without overlap from other tracks. For a given total activity (number of radioactive decays per second) in the object, a larger number of tracks can be resolved if the detector readout is faster or if the tracks are shorter and spread more evenly over the face of the detector. Certain track detector embodiments are based on CCD or CMOS cameras, and benefit by rapid progress in such cameras. For example, an ultrafast CMOS camera, capable of reading out $10^{10}$ pixels per second (10,000 frames per second at 1 megapixel per frame) is optionally utilized. The length of the track is optionally controlled by choosing the density of the material with which the beta particle interacts. In the configurations of FIGS. 7a and 7b, for example, there is a lot of free space between interaction points, so the tracks are optionally several millimeters long. In FIG. 7c, the interaction is in silicon (density 2.3 g/cc), so the track length is optionally less than 1 mm for the beta energies of interest in medical imaging, and in iQID devices, scintillators with densities of 5 g/cc or more are optionally used, giving even shorter track lengths and higher allowed event rates.

Example 3: Beta Particle Detection in Microtome and Macrotome Systems

The detection schemes described above are useful in microtome and macrotome systems, where thin slices (e.g., 1 μm to 100 μm thick) are sequentially removed from a sample. Conventional microtome and macrotome systems rely on a costly and time consuming tape transfer process for determination of beta particle emitting compositions within the object, where each section is removed from the object and section-by-section analysis is performed. In contrast, the present invention provides techniques for determination of the beta particle source distribution within the object directly, whether the object is provided in a macrotome or a microtome system, such as a cryomacrotome system or a cryomicrotome system.

Figure 11:
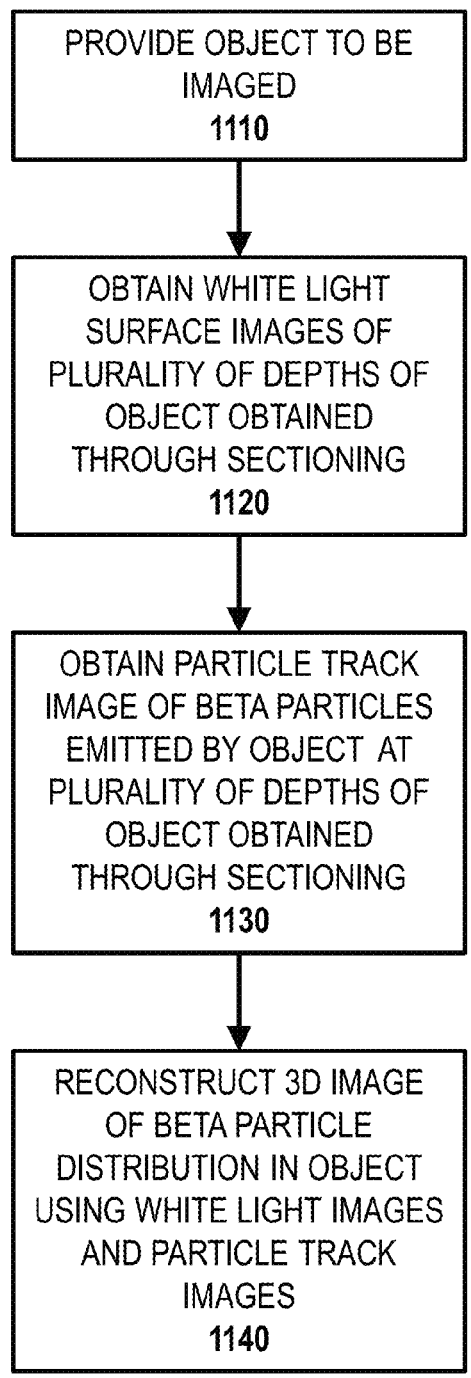
FIG. 11 provides an overview of a method for reconstructing a particle distribution.

FIG. 11 provides an overview of an exemplary method embodiment of this aspect. First, the object, such as a tissue sample, is provided (1110). Optionally, white-light images of a plurality of surfaces of the object are obtained at a plurality of depths obtained through sectioning (1120). Although obtaining white-light images is not required by all embodiments of the invention, useful information, such as anatomical and/or compositional information, can be obtained through the white-light images and can provide advantages thereby. As the object is being sequentially sectioned, a plurality of beta particle track images are obtained at a plurality of depths obtained through sectioning (1130). For example, in embodiments, this process occurs by placing a particle track detector at or near the surface of the object and imaging beta particles emitted from the object prior to slicing the object to observe a deeper depth within the object. After white-light images and beta particle track images are obtained, a 3D image of the beta particle distribution within the object is reconstructed using the obtained particle track images and white-light images (1140).

Figure 12:
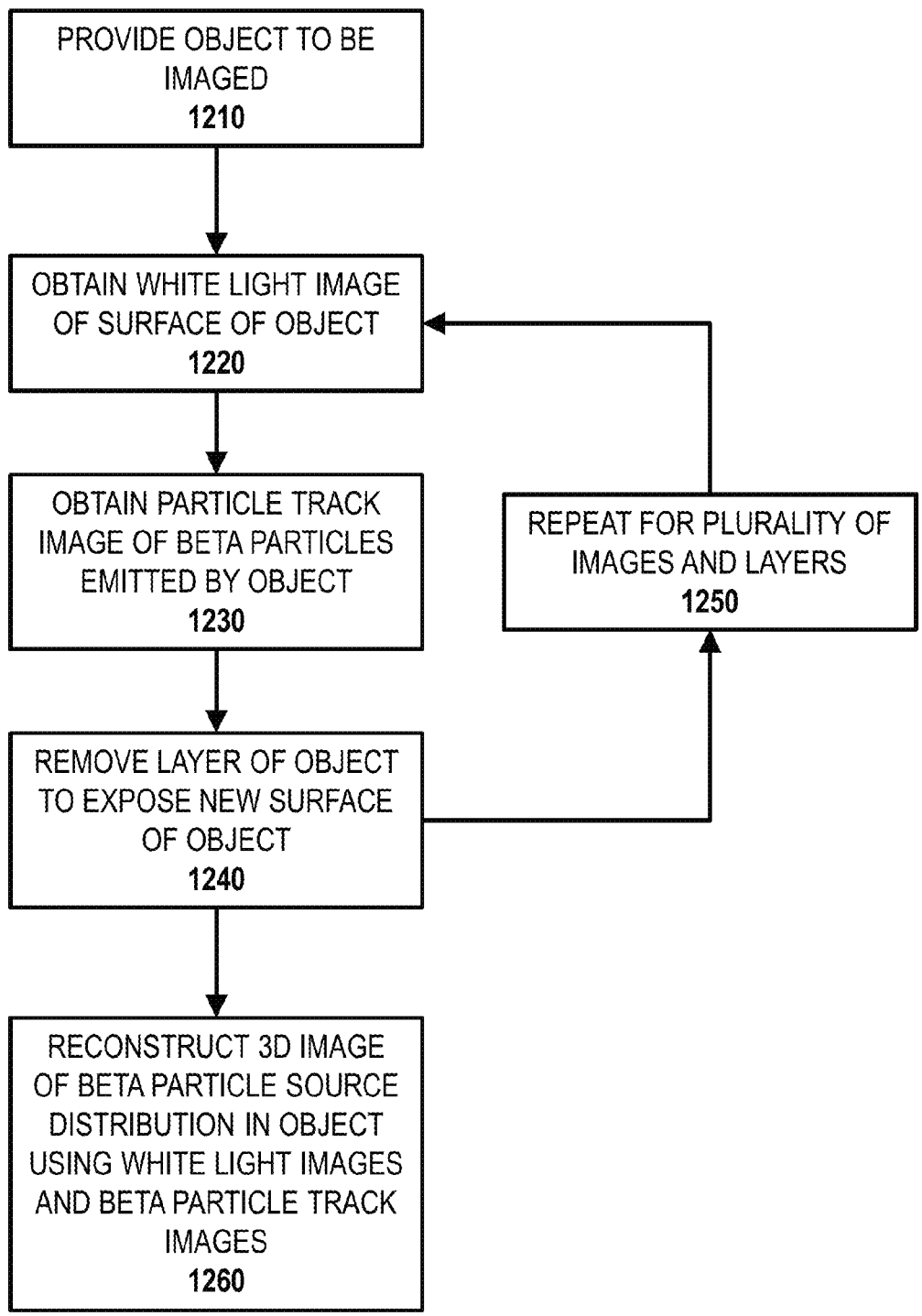
FIG. 12 provides an overview of a method for reconstructing a particle distribution using a tomographic type method.

FIG. 12 provides a more detailed overview of a method embodiment of this aspect. Again, the object, such as a tissue sample, is provided (1210). Next, a high resolution white-light image of a surface of the object is obtained (1220). Following this, beta particle track images of beta particles emitted by the object are obtained (1230). Note that for some embodiments, the order of collection of white-light images and beta particle track images is reversed and the beta particle track images are obtained prior to the collection of the white-light image. After both the white-light image and beta particle track images are collected, a layer of the object is removed, such as by a slicing mechanism, thereby exposing a deeper surface of the object (1240). In some embodiments, a section formed by slicing is removed for subsequent analysis. In other embodiments, a section formed by slicing is disposed of. In yet other embodiments, the layer of the object is removed by a mechanism other than slicing, such as by a milling type machining technique. If desired, the processes of obtaining white-light images of the surface, track images of beta particles emitted by the remaining object and removing a layer of the object to expose a deeper surface are repeated a plurality of times (1250), such as a sufficient number of times to obtain white-light images and beta particle track images throughout the entire range of depths of the object. In embodiments, a step of removing the last layer of the object is optionally omitted. After the white-light images and beta particle track images are obtained, a 3D image of the beta particle distribution within the object is reconstructed using the obtained particle track images and white-light images (1260). In some embodiments, the 3D reconstruction takes place using one or more particle track images and one or more white-light images and is updated as each subsequent particle track image and white-light image are obtained. In some embodiments, the 3D reconstruction takes place only after all particle track images and all white-light images are obtained.

Using these techniques provides significant benefits for determination of beta particle distributions within an object over conventional methods. First, the costly and time consuming step of tape transfer of sections is eliminated, as the white-light images and beta particle track images can be obtained directly from the sequentially exposed surfaces of the object as layers of the object are removed. Second, the method of determining beta particle source distributions provided above can be utilized, which provides additional advantages, such as improvements in speed and accuracy, compared with conventional techniques where beta particle images of tape transferred sections are obtained. Third, as the beta particles are detected directly at the object and not at another detection location, as is the case in conventional tape transfer techniques where the sections need to be removed and placed in a second device for beta particle detection, the opportunity for contamination of the sample or sections is reduced.

Figure 13:
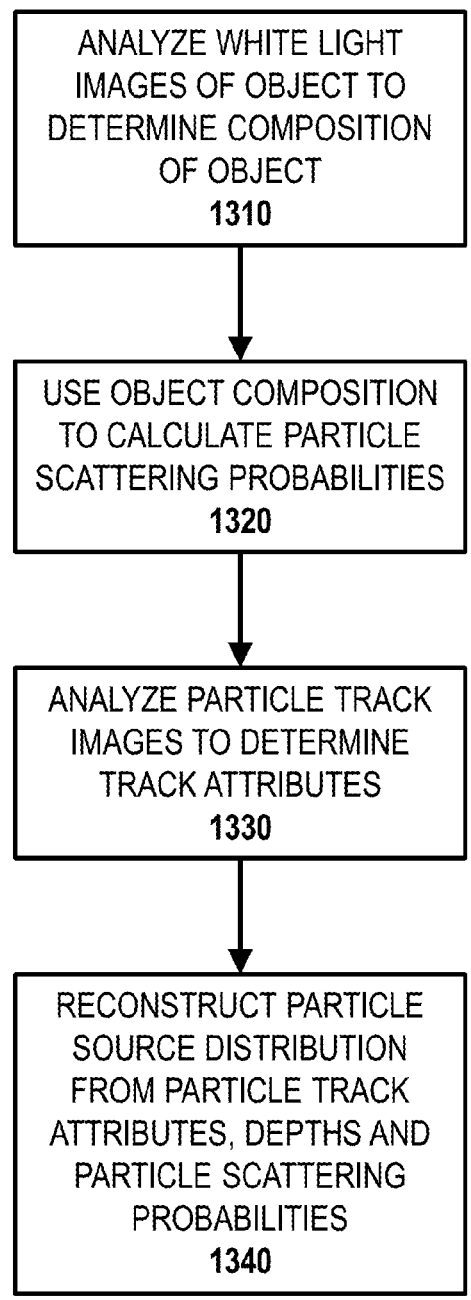
FIG. 13 provides an overview of a method for reconstructing a particle distribution.

FIG. 13 provides an overview of a method embodiment for reconstructing a 3D image of the beta particle distribution within an object from a plurality of white-light images and particle track images. First, the white-light image(s) are analyzed to determine a composition or anatomy of various portions of the object (1310). This information can be useful, for example, to calculate beta particle propagation probabilities or probability distributions throughout the object (1320), as different types of materials or tissues can affect the propagation probability of beta particles as they pass through the object. Depending on the object, tissue or material involved, however, in embodiments, this step may be omitted, particularly if the beta particle propagation probability within the object, tissue or material is invariant or substantially invariant. Next, the particle track images are analyzed to determine attributes of the particle track (1330). For example, in an embodiment, a direction of travel and position of each beta particle as it entered the particle track image detector are determined. This trajectory and/or position/direction information (i.e., track attributes) and particle track image depth are combined with the beta particle propagation probabilities to determine the distribution of the source of beta particles within the object (1340), and are optionally processed to create an image showing the distribution of the source within the object. In one embodiment, each beta particle trajectory and/or position/direction information and the beta particle propagation probabilities or probability distributions are used in a list-mode maximum-likelihood expectation-maximization algorithm to determine a 3D distribution of the source of beta particles. FIG. 4 provides an overview of one embodiment for determination of the position of the source of a beta particle.

It will be understood by the skilled artisan that, although a suitable white-light image can be obtained within a short period of time, such as less than 1 second, a suitable particle track image may take a longer amount of time to obtain a sufficient number of beta particle track events to accurately determine the distribution of beta particle emitting material within the object of interest. For example, in one embodiment, the beta particle track image is obtained over a period of hours, such as a period of between 4 and 6 hours or even longer.

Figure 14:
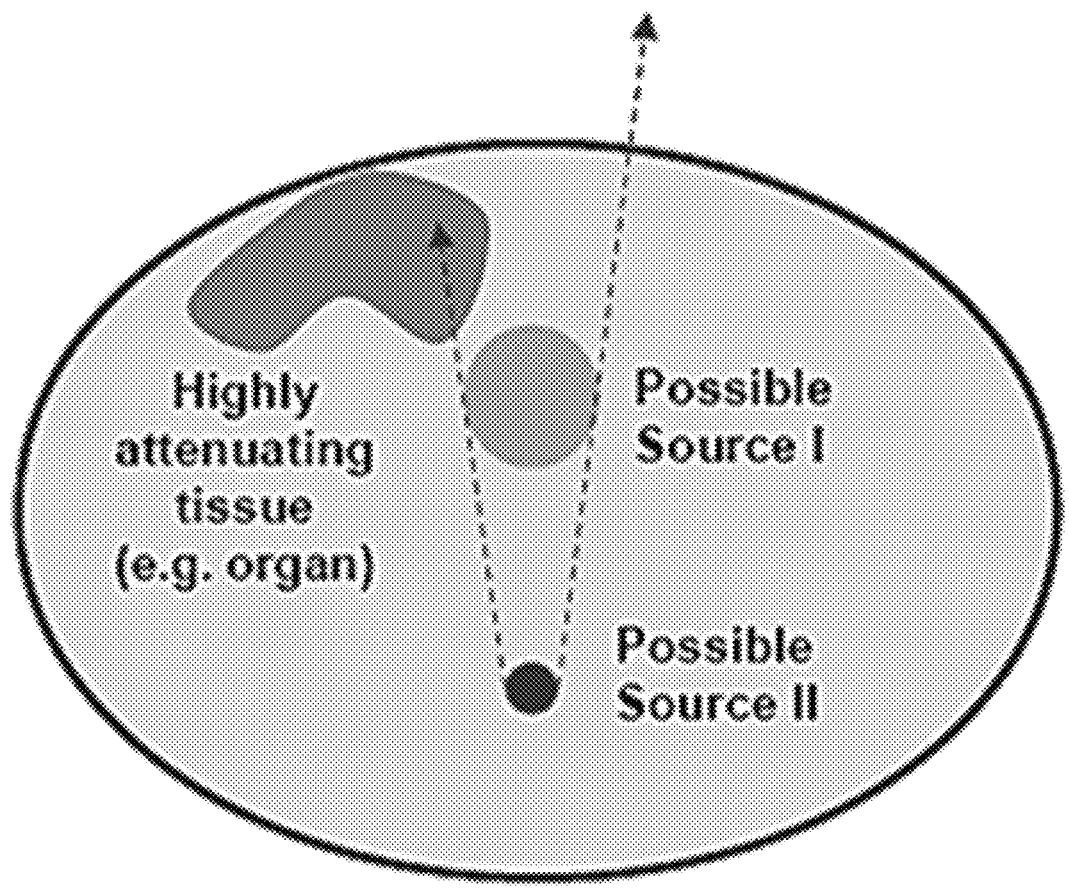
FIG. 14 provides a schematic depiction of a cross sectional view of an object including a source of particles.

FIG. 14 provides a schematic depiction of a cross sectional side view of an object, showing an example of a portion of the object that is highly attenuating or scattering for beta particles. Having this information, such as obtained by analysis of a white-light image, prior to reconstructing the 3D distribution of beta particle sources within the object is advantageous for accurately determining the location and concentration of beta particle emitting material within the object, such as a radiopharmaceutical within a tissue.

In addition, FIG. 14 provides an example of an issue that is overcome by the techniques described in this example. For example, in some embodiments, two different locations within an object are potential sources of beta particles that can provide identical particle track image information. Source I in FIG. 14 is a source closer to the surface and larger in volume but containing a lower concentration of beta particle emitting material; Source II in FIG. 14 is a source deeper within the tissue and smaller in volume and containing a higher concentration of beta particle emitting material. Using the techniques described in this example, it can be determined whether Source I is the actual source or whether Source II is the actual source, as layers of the material are subsequently removed and the object reimaged.

Figure 15:
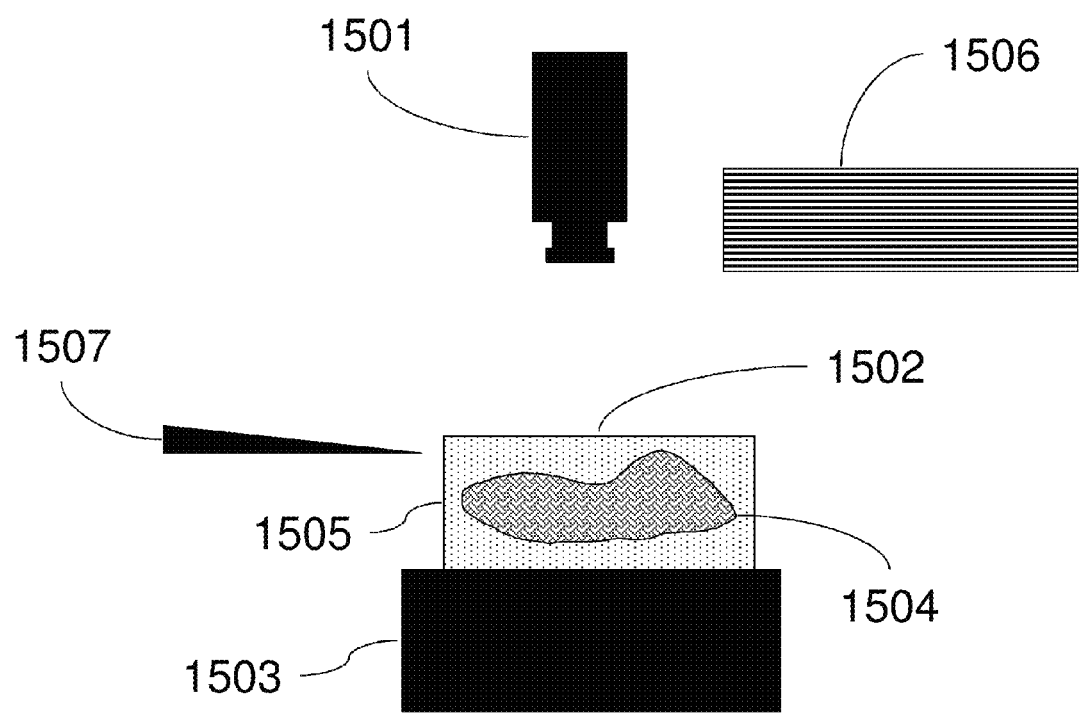
FIG. 15 provides a schematic illustration of a device for obtaining layer-by-layer data collection of white-light images and/or particle track images at a plurality of depths through an object.

FIG. 15 provides a schematic illustration of a device for obtaining layer-by-layer data collection of white-light images and/or particle track images at a plurality of depths through an object. The device shown in FIG. 15 includes a high resolution camera 1501, used for obtaining white-light images of a surface of a sample 1502 mounted on a sample holder 1503. In embodiments where white-light images are not required, the device optionally does not include a camera. Here, sample 1502 includes a tissue 1504 embedded in a containing material 1505. The device also includes a particle track detector 1506, used in the determination of beta particle trajectories. The device also includes a blade 1507 for slicing sample 1502 to remove sections and reveal deeper surfaces. Camera 1501 and/or particle track detector 1506 are optionally mounted on a robotic system to sequentially place each at the appropriate location for collecting data. For example, in one embodiment, camera 1501 is positioned at a fixed location such that it can image the exposed surface of the object and particle track detector 1506 is positioned on a movable mechanism to position track detector 1506 at/near the surface of sample 1502 in order to obtain beta particle track images and then move track detector 1506 away from the surface for a slicing or white-light imaging operation. In another embodiment, camera 1501 is positioned on a movable mechanism in order to obtain white-light images and then move camera 1501 away from the sample for a slicing or white-light imaging operation.

Although in the embodiment shown in FIG. 15 the particle track detector is of a size sufficient to obtain a particle track image of the entire exposed area of the sample, in embodiments, the particle track detector is smaller than the exposed area of the sample, for example, such that a plurality of particle track images would be needed for the entire exposed area of the sample. For such embodiments, the particle track detector and/or the sample holder are optionally mounted on movable stages such that relative motion between the sample and particle track detector can provide sequential particle track images of different portions of the exposed area of the sample in order to obtain a full set of particle track images for the entire exposed area of the sample.

Figure 16A:
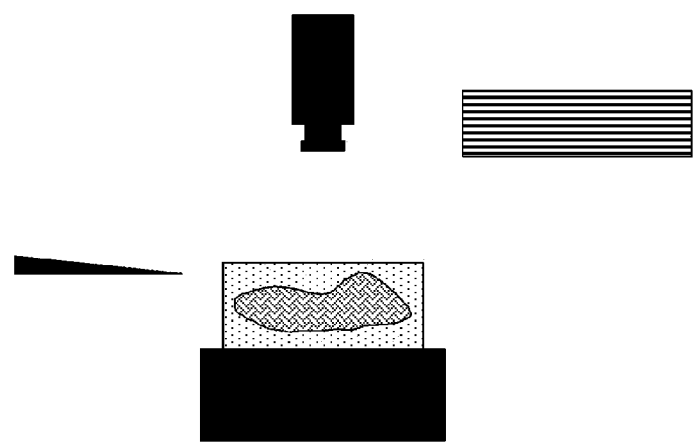
FIGS. 16A, 16B and 16C provide an overview of the device of FIG. 15 in operation.
Figure 16B:
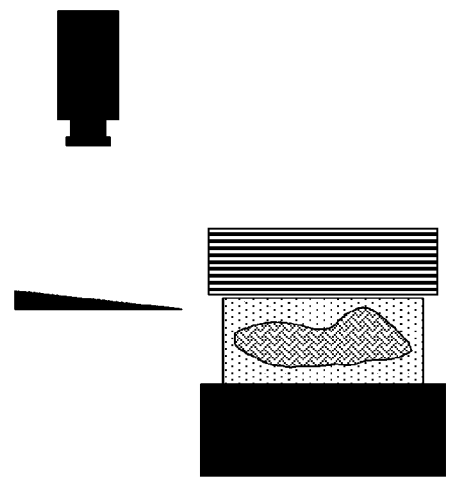
Figure 16C:
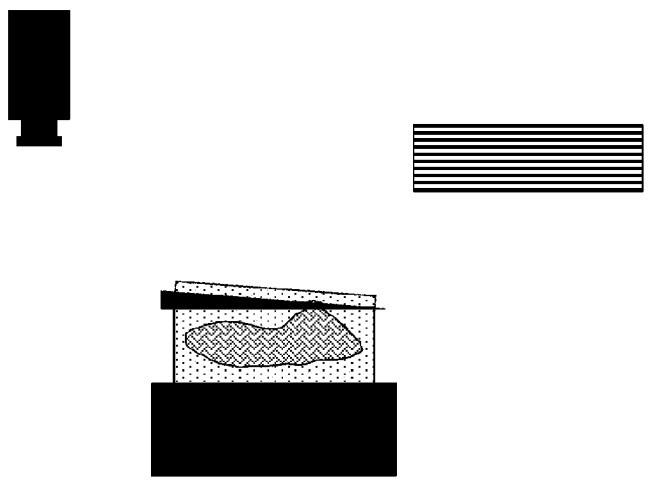

FIGS. 16A, 16B and 16C provide an overview of the device of FIG. 15 in operation. First a white-light image of the sample is obtained by the camera (FIG. 16A). Next, the camera is moved away from the sample and the particle track detector is moved to the surface of the sample to obtain a particle track image (FIG. 16B). Next, the particle track detector is moved away from the sample and the blade is used to slice and remove a section from the sample. Following this, the blade is retracted, the section removed, and the camera moved back toward the sample to obtain a white-light image of the surface exposed by removal of the section.

Figure 17:
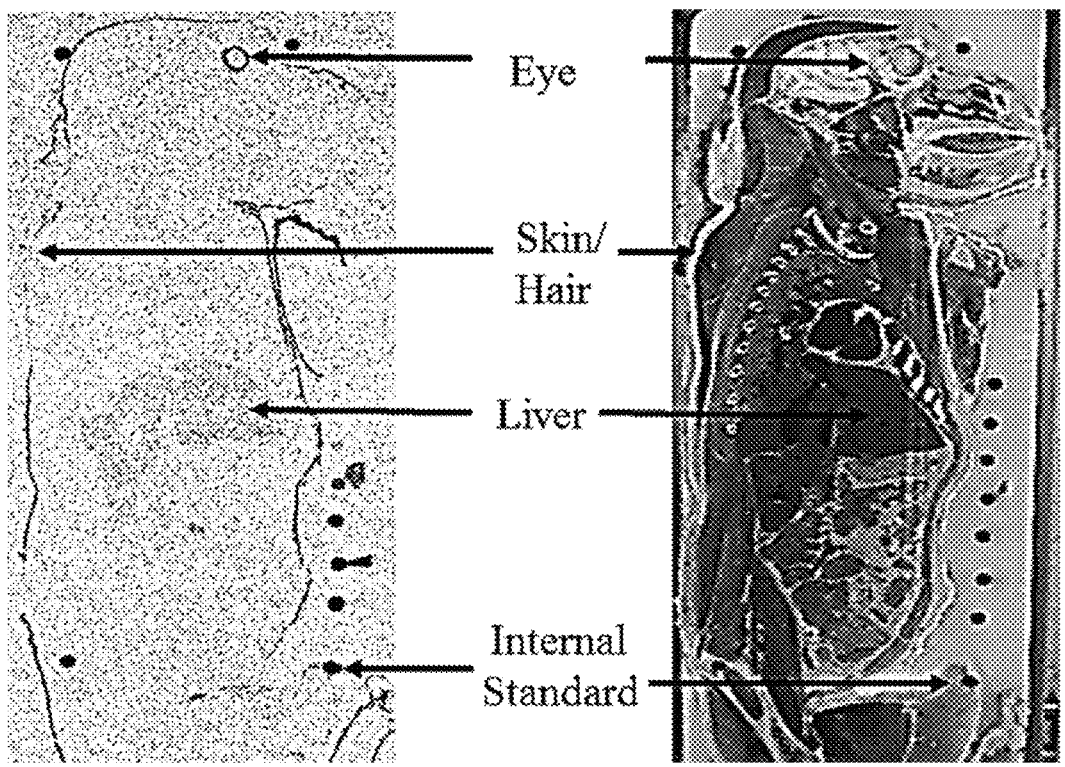
FIG. 17 provides an exemplary particle image and an exemplary white-light image of a tissue sample.

FIG. 17 provides an exemplary autoradiography samples including a beta particle image and a white-light image of a tissue sample. The beta particle image shown in FIG. 17 was obtained using a conventional beta particle detection technique.

REFERENCES

Miller, Brian W. 2011. Dissertation. High-Resolution Gamma-Ray Imaging with Columnar Scintillators and CCD/CMOS Sensors, and FastSPECT III: A Third-Generation Stationary SPECT Imager.

B. W. Miller, H. H. Barrett, L. R. Furenlid, H. B. Barber, and R. J. Hunter, "Recent advances in BazookaSPECT: Real-time data acquisition and the development of a gamma-ray microscope," *Nucl. Inst. Meth*. A, 591(1):272-275, 2008. PMCID: PMC2597870.

B. W. Miller, L. R. Furenlid, S. K. Moore, H. B. Barber, V. V. Nagarkar and H. H. Barrett, "System integration of FastSPECT III, a dedicated SPECT rodent-brain imager based on BazookaSPECT detector technology," *IEEE Nucl. Sci. Symp. Conf. Record*, 4004-4008, 2009.

B. W. Miller, H. B. Barber, L. R. Furenlid, S. K. Moore and H. H. Barrett, "Progress in BazookaSPECT," *Proc. SPIE*, 7450:7450C, 2009. PMCID: PMC3033223

B. W. Miller, H. B. Barber, H. H. Barrett, Z. Liu, V. V. Nagarkar and L. R. Furenlid, "Progress in BazookaSPECT: high-resolution dynamic scintigraphy with large-area imagers," *Proc. SPIE* 8508:85080F, 2012.

B. W. Miller, H. H. Barrett, H. B. Barber and D. W. Wilson, "Gamma-ray microscopy using micro-coded apertures and Bazooka SPECT, a low-cost, high-resolution image intensifying gamma camera," 334366:158, Annual Meeting of the Society of Nuclear Medicine, Washington, D.C., Jun. 2-6, 2007.

B. W. Miller, D. R. Fisher, L. R. Furenlid, B. M. Sandmaier, J. M. Pagel, A. Kenoyer, S. Frost, D. S. Wilbur, D. Hamlin, E. Santos, O. Press, "Digital autoradiography with the iQID alpha camera", Targeted Alpha Therapies Conference (submitted)

U.S. Pat. No. 7,928,397, U.S. Pat. No. 8,519,338

L. Parra and H. H. Barrett, "List-mode likelihood—EM algorithm and noise estimation demonstrated on 2D-PET," IEEE Trans. Med. Imag., MI-17:228-235, 1998.

Figure 18:
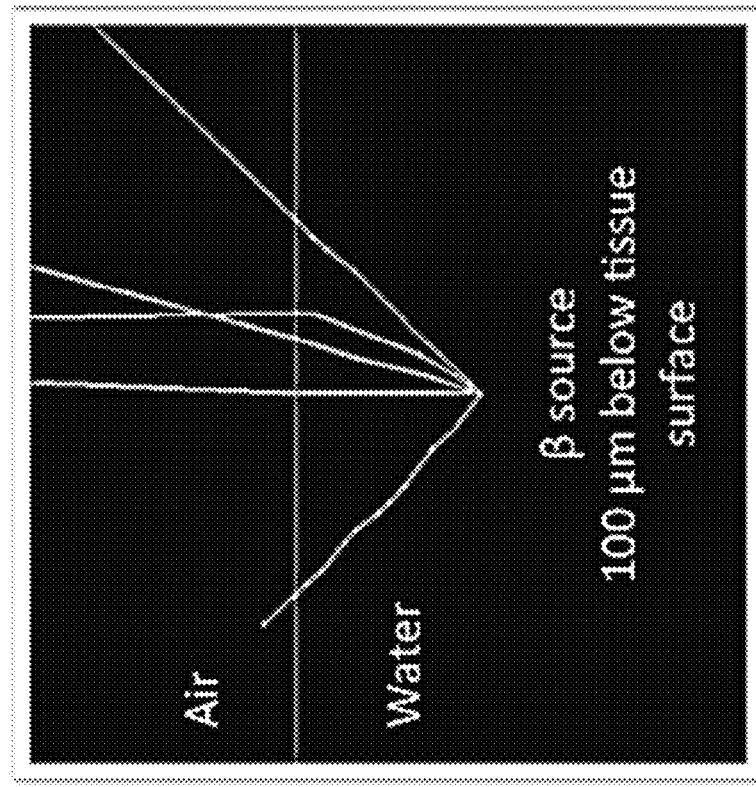
FIG. 18 illustrates travel paths of alpha particles and beta particles. While alpha particles tend to travel in straighter lines than beta particles, beta particles tend to have a longer range.
Figure 18:
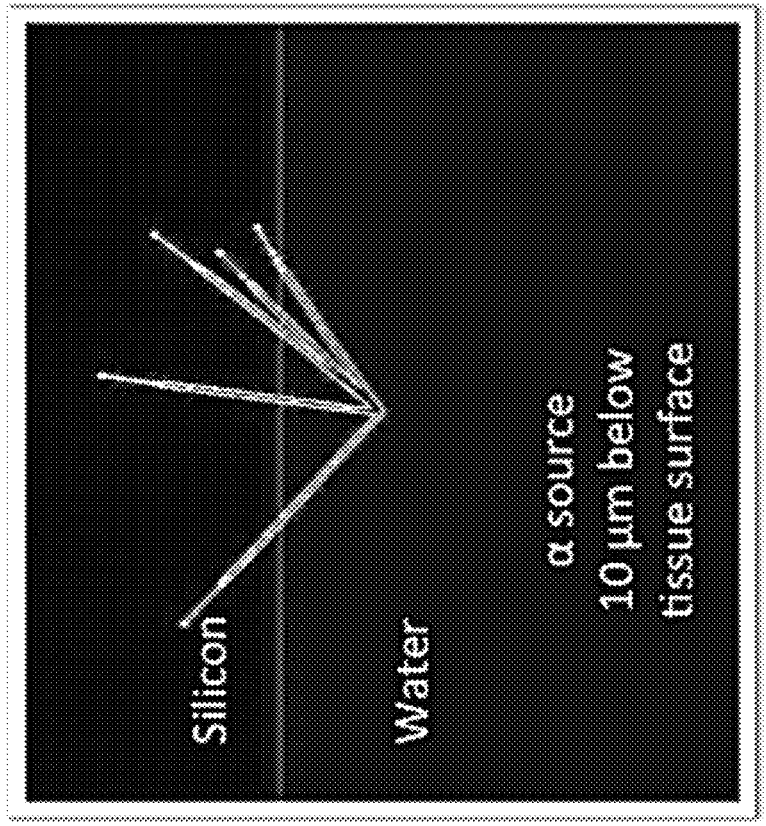

Example 4: Alpha Emission Tomography (3d Autoradiography) with Track Information Both beta and alpha particles have advantages and disadvantages for imaging applications. For example, as shown in FIG. 18, alpha particles can travel in straighter lines than beta particles and can have a range of approximately 45 μm in water. This sets a limit for the thickness of a specimen that can be imaged with alpha particles. However, because alpha particles propagate along straighter lines than beta particles, their original direction of propagation can be estimated with greater accuracy, potentially leading to higher resolution. On the other hand, beta particles are more scattered (they propagate along tracks that are more irregular than those for alpha particles) but they have a longer range. With beta particles, it is possible to image thicker specimens, but higher scattering might result in reduced resolution. It should be noted that, for any given application, there are other reasons (besides specimen thickness and resolution) to favor one type of particle as opposed to the other. This includes, but is not limited to, the target organ (or disease) and its radiotracer uptake; the cost, washout rate, and half-life of the radiotracer; availability of accurate statistics models for particle propagation; and computing hardware and software (algorithms) that implement such models.

The applicability of the present methods and devices for 3D autoradiography via alpha particle detection was experimentally evaluated using track detection. Specifically, track detection of alpha particles is achieved using a pair of thin phosphor foils having a thickness of 3 microns spaced apart from each other by 125 microns. The phosphor foils are provided proximate to the source of alpha particles such that interaction of emitted alpha particles with the phosphor foils results in generation of optical signals that are detected via imaging using a two-dimensional optical detector.

The image data from the two-dimensional detector is analyzed to obtain attributes of the detected alpha particles, such as the position of the particle at the start of the particle track, the direction of travel of the particle and/or energy deposited in the detector. In an embodiment, for example, the attributes for each detected particle is stored in an attribute list, such as a 4D grid of bins. The 3D distribution of the source of particles is subsequently reconstructed using the attributes obtained from the imaging data, for example, using a list-mode maximum-likelihood expectation-maximization algorithm. In an embodiment, for example, reconstructing the 3D distribution of the source of alpha particles is carried out by calculating a probability density function for each of a plurality of locations within the source of particles.

Example 5: Directional Charged-Particle Detector with a Two-Layer Ultrathin Phosphor Foil Current charged-particle detectors are able to estimate the position and energy of a particle, but not its direction. This example is aimed at a detector capable of measuring the direction of a charged particle as well as its position. The detector uses an image intensifier and a lens-coupled CMOS (complementary metal-oxide-semiconductor) camera to capture the scintillation light excited by a charged particle traversing a phosphor assembly. The phosphor assembly is made of two layers of ultrathin phosphor foils separated by an air gap or a gap of other materials. The performance of the detector is illustrated by simulation, theory and experiment.

I. Introduction

Radioisotopes that emit alpha or beta particles are widely used in biology, pharmacology and radionuclide therapy. The current technique for charged-particle imaging, autoradiography, is two-dimensional, ex vivo imaging of thin slices. One can get the three-dimensional distribution of the radioisotope by imaging multiple thin slices and coregistering them. Charged-particle emission tomography, a direct three-dimensional autoradiography technique, would allow imaging of thick sections, avoid registration issues and increase laboratory throughput. Emission tomography of alpha particles ($\alpha$ET) and beta particles (BET) would facilitate radioisotope distribution studies and microdosimetry. In vivo $\alpha$ET and BET are possible in a small-animal window chamber, clinically for superficial lesions, and potentially endoscopically. A new concept is described below for a charged-particle detector that is able to provide directional information and position, hence enable $\alpha$ET and BET.

II. System Configuration

Figure 19:
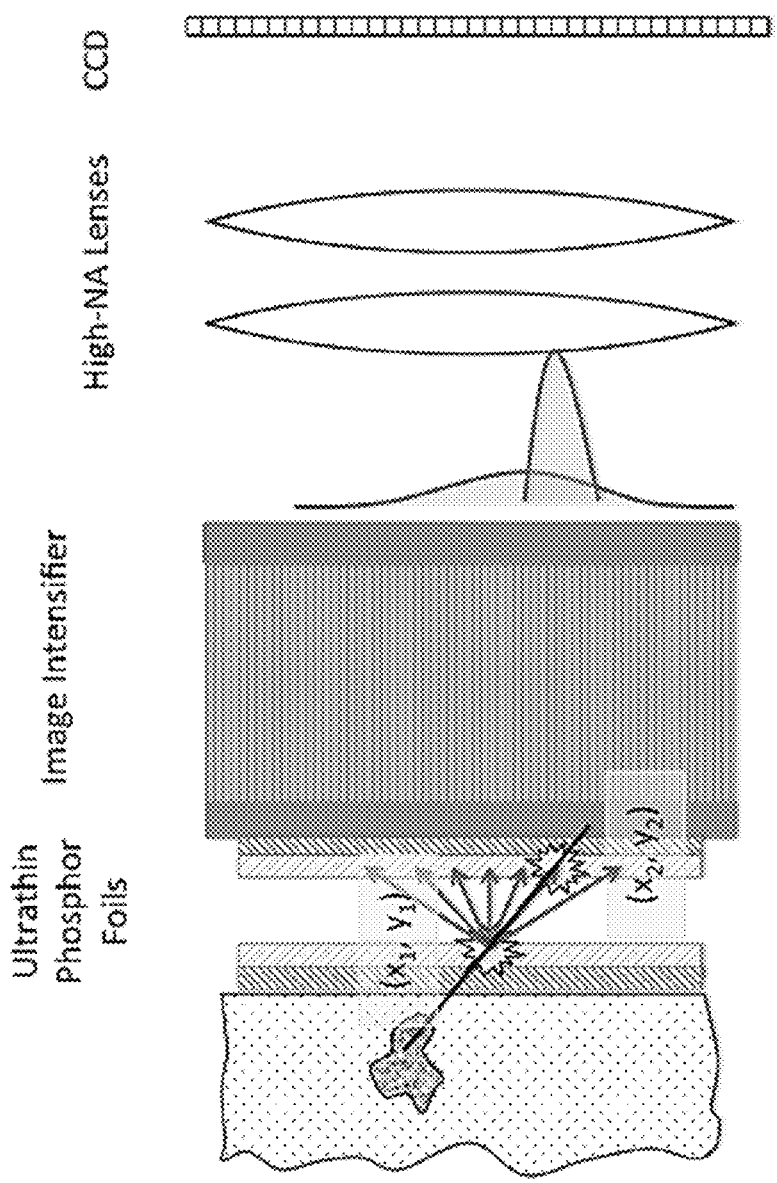
FIG. 19 provides an illustration of a directional charged-particle detector comprising a 2-layer ultrathin phosphor foil assembly used to detect two interaction points, which can be used to get directional information.

FIG. 19 shows a directional charged-particle detector consists of two layers of ultrathin phosphor foils separated by an air gap. A charged particle passes through the phosphor and deposits some small portion of its kinetic energy there. The process is accompanied by production of visible light. The interaction with the first phosphor layer produces only a small angular deflection of the charged particle, which then passes on to the second layer and produces light there also. The light produced at the first layer spreads out more than that produced by the second phosphor layer, which can be used to determine at which layer each flash of light was produced. The two positions can be estimated from the image of the light produced by each particle on the camera. With the two positions and the air-gap separation, the direction of the particle can be estimated.

The ultrathin phosphor foil consists of a 3.5 µm thick layer of P43 phosphor powder coated on a 3 µm thick clear Mylar foil (Applied Scintillation Technologies). The two phosphor foils are parallel to each other, and the two phosphor sides face each other. The air-gap separation between the two phosphor foils is about 125 µm. The image intensifier (ProxiVision) uses a 2-stage microchannel plate, which amplifies the excited light signals to achieve sufficient sensitivity. Two F/1.2 camera lenses of 50-mm focal length coupled together to form an image of the intensifier output screen at unity magnification on an ultrafast CCD camera (Phantom V1210, Vision Research Inc.). This camera has 1280×800 pixels with 28 µm pitch and can operate at a speed of 10,000 frames per second. The light-capturing system setup is similar to that of the BazookaSPECT imager [1]. The entire system is enclosed in a light-tight box, and the ambient light background in the box is negligible.

III. Monte Carlo Simulation of the Detector

The Geant4 toolkit is used to perform simulations for an ideal monoenergetic charged-particle point source sus-pended in air 20 µm away from our 2-layer phosphor-foil assembly. The simulated energies are 5.24 MeV for the alpha source and 1.00 MeV for the beta source. The normal of the phosphor foil away from the source is defined as the +z axis. The simulated point source emits charged particles isotropically with a zenith angle $\theta$ (with respect to the normal of the phosphor foil), $0 \le \theta < \pi/4$. The source is surrounded by air. Charged-particle information at the four phosphor boundaries are recorded (including Mylar-phosphor boundary and phosphor-air boundary in the two layers). Simulation results are listed in Table 1. The energy absorbed at the first (second) phosphor layer is denoted as $\Delta E_1$ ($\Delta E_2$) in Table 1; $\Delta r_1$ is the projection of the distance between the particle's entrance point and exiting point of phosphor layer 1 on to the phosphor plane; $\Delta r_2$ is that of phosphor layer 2. A unit vector $s_i$ is used to describe the initial direction of a particle when it enters the first phosphor layer. Unit vector s is used to represent the direction determined by the center of a particle track in phosphor layer 1 and that in phosphor layer 2. The angular deviation between $s_i$ and s is $\Delta\theta$. The angular deviation described here is from scattering of charged particles within phosphor layer 1. As pre-calculation data-selection criterion, $\Delta r_1$ and $\Delta r_2$ are accepted only when they are both less than 100 µm in length. Out of $10^6$ alpha decay events simulated, 996,294 of them satisfy the criterion and are taken into account in the calculation of the results in Table 1. The number of selected events for beta particles is 973,764.

TABLE 1

Simulation results for alpha particles and beta particles. Landau($\mu$, $\sigma$) is a Landau distribution [2] with $\mu$ related to the peak location and $\sigma$ related to the width of the distribution.

|  | A | β |
|---|---|---|
| $\Delta r_1$ (µm) | 2.09 ± 0.87 | 2.16 ± 1.19 |
| $\Delta r_2$ (µm) | 2.11 ± 0.92 | 2.43 ± 1.94 |
| $\Delta E_1$ (keV) | 1182.1 ± 147.8 | Landau (1.5, 0.4) |
| $\Delta E_2$ (keV) | 1501.7 ± 283.2 | Landau (1.5, 0.4) |
| $\sigma(\Delta\theta)$ | 2.23° | 6.86° |
| acceptance percentage | 99.63% | 97.38% |

The results indicate that it is appropriate to use two spots, $(\hat{X}_1, \hat{Y}_1)$ and $(\hat{X}_2, \hat{Y}_2)$, to represent the interaction location of a particle with the two phosphor layers, because $\Delta r_1$ and $\Delta r_2$ are small compared to the thickness of the air gap. The energy deposited determines the number of optical photons generated in the phosphor. A previous paper mentioned that the P43 ultrathin phosphor produces 350 photons per 10 keV on average [3]. Therefore, on average an alpha particle produces more than 35,000 photons in each phosphor layer. For fast beta particles, the energy deposition of a beta particle can be described as a Landau distribution (Landau ($\mu$, $\sigma$)), with $\mu$ related to the peak location and a related to the width of the distribution. For one layer of 3.5 µm P43 phosphor, it is estimated that each incident beta particle produces about 53 optical photons since the location parameter of the Landau distribution is about 1.5 keV. The angular difference between $s_i$ and s, AB, has two degrees of freedom. If $\Delta\theta$ is represented by $(\Delta\theta_x, \Delta\theta_y)$, then $z=2(1-\cos(\Delta\theta)) \approx \Delta\theta_x^2 + \Delta\theta_y^2$ is a chi-square distribution with two degrees of freedom. By fitting the simulation results, the standard deviation of $\Delta\theta_x$ is estimated to be 2.23° for alpha particles and 6.86° for beta particles.

IV. Theoretical Analysis of Detector Performance

A. Analysis of a single foil. The analysis is started by considering just one phosphor foil, some distance from the image intensifier and illuminated by a stream of charged particles. Because of the strong scattering of light in the phosphor, it can be treated treat as a Lambertian emitter. The distribution of irradiance on the face of the intensifier (which we denote as the plane z=0) from a Lambertian phosphor in the plane $z=-z_p$ is proportional to $\cos^4\theta_{opt}$, where $\theta_{opt}$ is the angle between the normal to the two planes and the direction of light propagation.

Suppose there are K beta particles passing through the phosphor and event k (k=1, ..., K) produces a small spot of light at a point on the phosphor specified by the 2D vector $r_k$. The irradiance on the intensifier at point r is given by:

$$E(r|r_k) \propto \cos^4\theta_{opt} = \frac{z_p^4}{[|r_k - r|^2 + z_p^2]^2}. \quad (1)$$

Suppose the optical photons generated by the $k^{th}$ beta interaction produce a total of $J_k$ photoelectrons. The probability density function (PDF) for a particular electron, say the $j^{th}$, to be produced at $r=r_{kj}$ is $$pr(r_{kj}|r_k) = \frac{z_p^4/\pi}{[|r_k - r_{kj}|^2 + z_p^2]^2}. \quad (2)$$

In an idealized representation of the data, the set of all photoelectron positions is known $\{r_{kj}; j=1, \ldots, J_k\}$, as well as $J_k$ itself. From these data, denoted as $G_k$, it is desired to estimate the interaction position $r_k$. The maximum-likelihood (ML) estimate of the position of interaction is [4]:

$$\hat{r}_k = \underset{r_k}{\operatorname{argmax}} \sum_{j=1}^{J_k} \ln\left[\frac{z_p^2/\pi}{[|r_k - r_{kj}|^2 + z_p^2]^2}\right], \quad (3)$$

where the hat denotes an estimate.

Figure 20:
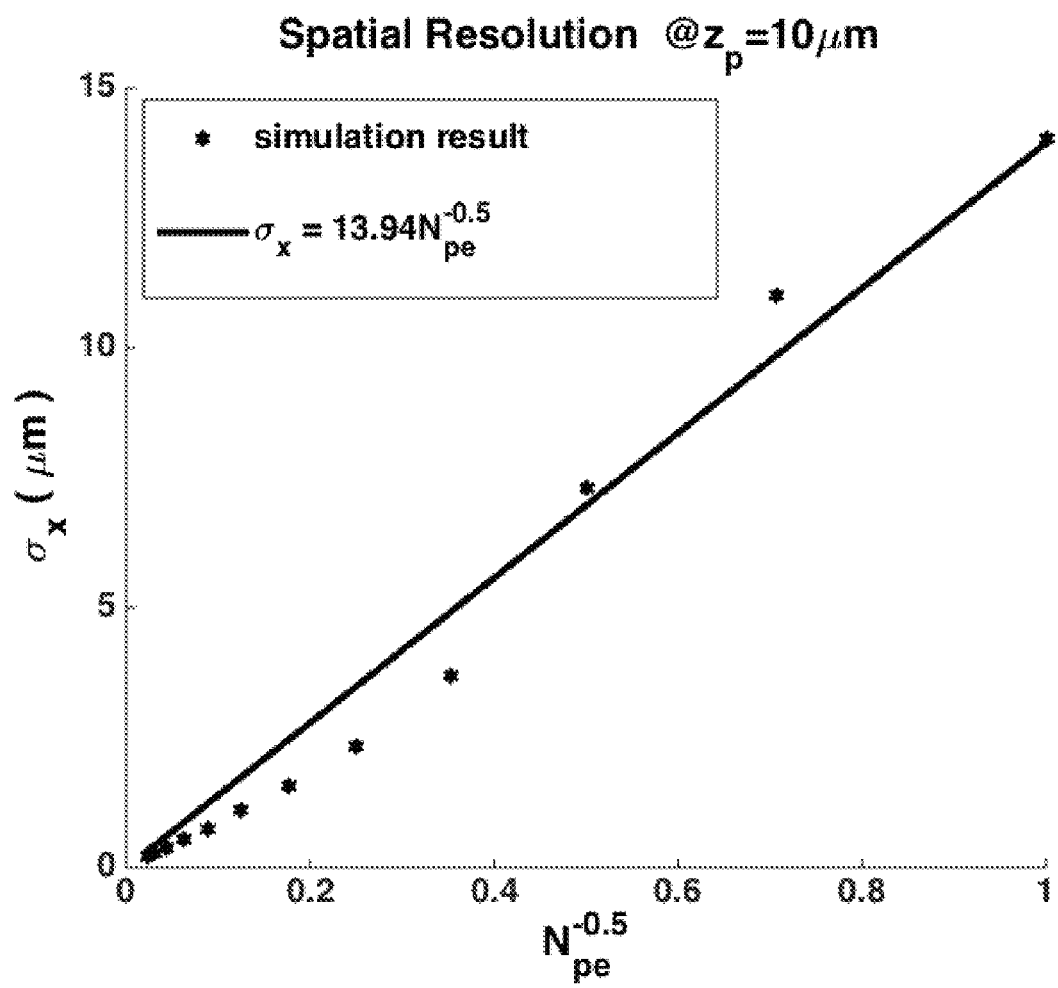
FIG. 20 provides a graph showing the estimation of spatial resolution for a single-foil detector, when the phosphor foil is 10 µm away from the face of the intensifier.

The estimation is repeated 1000 times and the standard deviation used as an indicator of the spatial resolution of a single-foil detector. The spatial resolution is proportional to $z_p$ and inversely related to the square root of $N_{pe}$, where $N_{pe}$ is the average number of detected photoelectrons in each event. FIG. 20 shows the relation between $\sigma_x$ and $N_{pe}$, where $\sigma_x$ is the standard deviation of the estimated x-coordinate; note that $\sigma_y=\sigma_x$ since the detector has rotational symmetry. From the plot, the relation between $\sigma_x$, $N_{pe}$ and $z_p$ can be written as:

$$\sigma_x = \frac{A}{\sqrt{N_{pe}}} \cdot z_p, \quad (4)$$

where $A \approx 1.39$.

B. Analysis of a Two-Foil Detector.

Now consider two foils, one in the plane $z=-z_1$ and the other in the plane $z=-z_2$, where $z_1 > z_2 > 0$. Thus the beta particle first encounters foil 1, then foil 2. Two interaction positions are specified with 2D vectors $r_1$ and $r_2$. The two interaction positions are related by $$r_2 = r_1 + s_\perp d \quad (5)$$

where $d=z_1-z_2$ and $s_\perp$ is a 2D vector in the direction of $r_2-r_1$; if a 3D unit vector is defined $$s \equiv (s_x, s_y, \sqrt{1-s_x^2-s_y^2})$$

in the direction of particle travel between the two interaction positions, then the 2D vector $s_\perp \equiv (s_x, s_y)$ can be interpreted as the projection of the 3D unit vectors onto a plane perpendicular to the z axis. Note that $s_\perp$ is not a unit vector.

The goal is to estimate the 2D interaction position $r_1$ and the 3D unit vector $s_i$, which determine the position and direction of an incident charged particle at the plane of foil 1, but because of the random deflection of the particle in the first foil, the incident direction is not directly measurable. According to the discussion in Section III, however, s can be used as an approximation of $s_i$, so it will suffice to estimate the two 2D vectors $r_1$ and $s_\perp$.

If there are ML estimates of $r_{1k}$ and $r_{2k}$ for each event k, the maximum-likelihood invariance theorem can be invoked which states that an ML estimate of a function of a parameter is that same function of the ML estimates of the parameter. The ML estimate of $s_{\perp k}$ is thus $$\hat{s}_{\perp k} = \frac{\hat{r}_{2k} - \hat{r}_{1k}}{d}. \quad (6)$$

Denote $\hat{\theta}_x$ as the angle between the plane y=0 and the direction of particle propagation, in which case $$\tan \hat{\theta}_x = \hat{x}_2 - \hat{x}_1/d.$$

The uncertainty of $\hat{\theta}_x$ is given by $$\sigma(\hat{\theta}_x) = \cos^2\hat{\theta}_x \cdot \frac{\sqrt{\sigma_{x1}^2 + \sigma_{x2}^2}}{d}. \quad (7)$$

As a preliminary step to study the angular resolution of a two-foil detector, assume that $r_{1k}$ and $r_{2k}$ can be estimated respectively with uncertainties given by equation (4), derived for single foils. The angular uncertainty is then found to be $$\sigma(\hat{\theta}_x) = \cos^2\hat{\theta}_x \cdot \frac{A}{\sqrt{N_{pe}}} \cdot \frac{\sqrt{t^2+1}}{t-1}, \quad (8)$$

where t is $z_1/z_2$. To get a feel for how big the angular uncertainty is, the case where $\cos \hat{\theta}_x=1$ is considered to get the upper limit of $\sigma(\hat{\theta}_x)$ is considered. The data in FIG. 20 is used to get A. The number of photons produced by the phosphor is discussed in Section III. Each foil produces on average 35,000 optical photons for an incident alpha particle. For betas, it is assumed the number of optical photons generated is 200, which is four times the number mentioned previously. This is possible by using a thicker phosphor or phosphor with higher light output efficiency. To get the number of photoelectrons produced in the image intensifier, the quantum efficiency of the photocathode is assumed as 30%. The uncertainty from particle scattering, $\sigma(\Delta\theta_x)$, is given in Section III. The combined angular uncertainty includes components from both scattering and the position estimations, added in quadrature. The results for alpha and beta particles are given in Table 2.

TABLE 2

Angular uncertainties of a 2-foil detector for alpha particles and beta particles.

|  | A | B |
| --- | --- | --- |
| $N_{pe}$ | 5250 | 30 |
| $\sigma(\theta_{\tilde{x}})$ | 1.14° | 15.13° |
| $\sigma(\Delta\theta_x)$ | 2.23° | 6.86° |
| $\sigma(\theta_x)_{tot}$ | 2.51° | 16.62° |

V. Experimental Results with Alpha Particles

Figure 21:
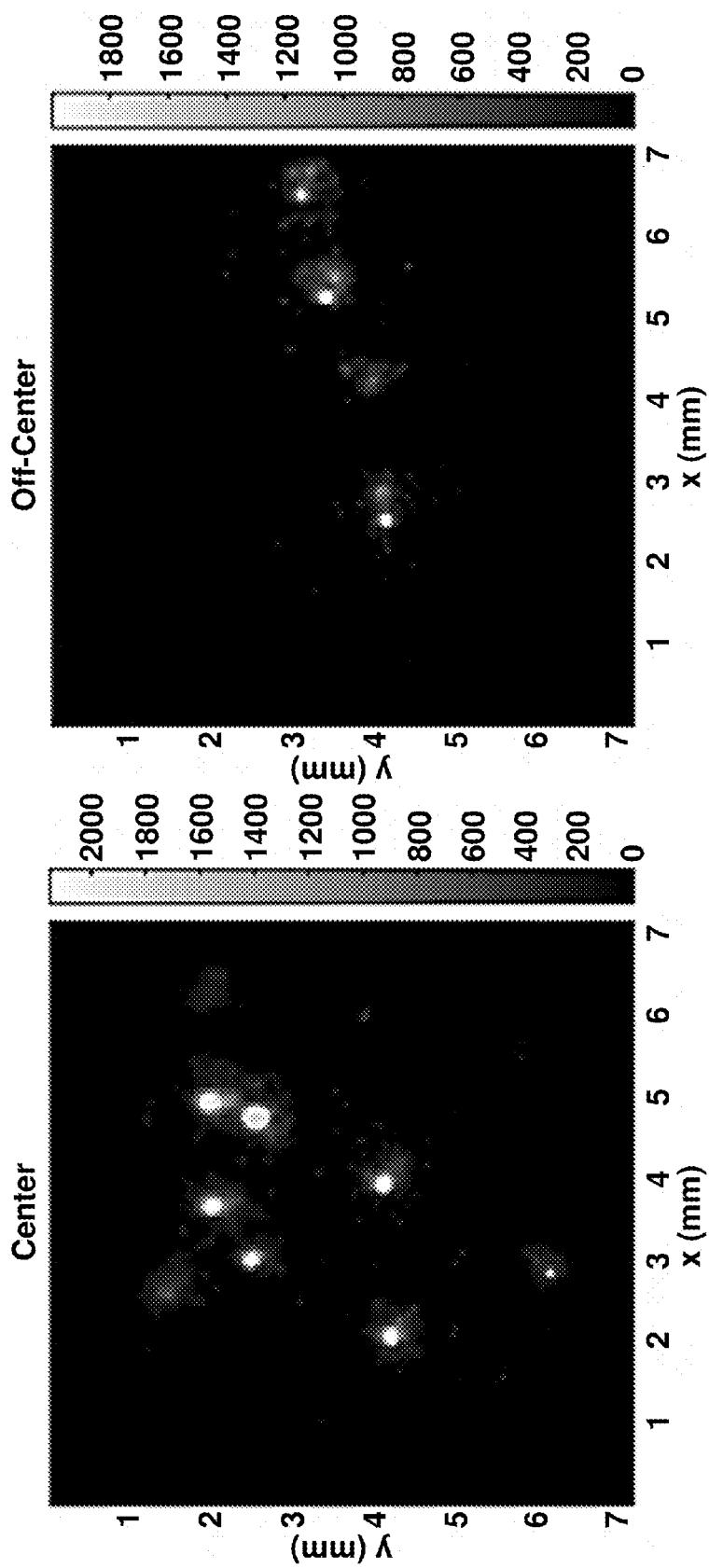
FIG. 21 provides plots of single-frame camera response of a 2-foil detector to an alpha source on-axis (left) vs. off-axis (right). There is clear separation between $(\hat{X}_1, \hat{Y}_1)$ and $(\hat{X}_2, \hat{Y}_2)$ when most of the alpha particles incident at an angle (right). Each blob in the figure is an interaction of an alpha particle in the phosphors.

FIG. 21 shows one frame of the detector response for an alpha source. For the experimental setup, a 6 kBq $^{239}$PU source shaped like a disk is used. The camera frame rate is 100 fps. The disk of the alpha source is parallel with the phosphor screen and is about 4 mm away from the phosphor screen. The size of the images in FIG. 21 is 256×256 pixels (7.2 mm×7.2 mm). The center of the phosphor assembly is approximately the center of the image. The diameter of the phosphor assembly is 6.6 mm. The figure on the left corresponds to the case of an on-axis source with the phosphor assembly, the two interaction spots $r_1$ and $r_2$ are very close to each other. When the source is moved off-axis, which implies that the alpha particles are incident on the phosphor assembly at larger angles, the two interaction points are well separated as shown in the figure on the right.

VI. Simulated BET Reconstructions

Using Geant4 simulated data, a beta particle-emitting object is reconstructed with additional directional information. A discretized field of view of size 512×512×40 voxels with 25 μm pitch is considered. The object is the Chinese character 'Ding' of size 1 mm×1 mm and thickness 100 μm, the center of which located at depth 400 μm away from the surface of the tissue. In the simulation, a detector of size 1 cm×1 cm is placed in contact with the tissue. Beta particles are emitted isotropically in all directions from the object. With 2 million events simulated, 0.51 million beta particles are collected by the detector and used in the reconstruction. For this simulation perfect estimation of the position and direction of each detected beta particle and prior knowledge of the depth of the object is assumed. This information is used in a Landweber algorithm for image reconstruction [4]. The center area of the reconstructed object is shown in FIG. 10 (top). For comparison, a conventional beta autoradiograph with 25 μm pixel size is shown in FIG. 10 (bottom).

VII. Conclusions

In this study, a directional charged-particle detector with a 2-layer ultrathin phosphor foil is introduced. When an alpha or beta particle passes through the detector assembly, each phosphor produces an optical image. The relative position of the two images changes with the incident angle. The preliminary estimation of the theoretical angular resolution of the detector is about 2.5° for alphas, and 16.6° for betas. Better angular resolution can be achieved by increasing the number of photoelectrons or reducing particle scattering in the phosphors. The phosphor thickness can be optimized by balancing light output and scattering. Additionally, scintillation materials with higher light output and lower density can be used and camera parameters can be incorporated into the theoretical framework. Accordingly, this theory can provide the probabilities needed to implement a List-Mode Maximum-Likelihood Expectation-Maximization (LMMLEM) [5] reconstruction algorithm and demonstrate charged-particle emission tomography with experimental data.

REFERENCES

[1] B. W. Miller, H. B. Barber, L. R. Furenlid, S. K. Moore, and H. H. Barrett, "Progress of BazookaSPEkCT," in SPIE Optical Engineering+Applications. International Society for Optics and Photonics, 2009, pp. 74 500C-74 500C.

[2] L. Landau, "On the energy loss of fast particles by ionization," J. Phys. USSR, 1944.

[3] L. Chen, L. S. Gobar, N. G. Knowles, D. W. Wilson, and H. H. Barrett, "Direct charged-particle imaging system using an ultra-thin phosphor: physical characterization and dynamic applications," IEEE Transactions on Nuclear Science, vol. 56, 2009.

[4] H. H. Barrett and K. J. Myers, Foundations of Image Science. Wiley N.Y., 2004.

[5] L. Parra and H. Barrett, "List-mode likelihood: EM algorithm and image quality estimation demonstrated on 2-D PET," IEEE Transactions on Medical Imaging, 1998.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for reconstructing a 3D distribution of a source of particles, the method comprising the steps of:
    providing said source of particles, wherein said particles comprise beta particles, alpha particles, positrons, or conversion electrons;
    repeating, for each of a plurality of said particles from said source, the steps of:
        recording an image of a particle track with a particle track detector;
        determining attributes of said particle track using said particle track image; and
        storing said attributes of said particle track;
    thereby generating attributes for each of said plurality of particles from said source; and
    reconstructing said 3D distribution of said source of particles using said attributes for each of said plurality of particles.

2. The method of claim 1, wherein said particle track detector comprises a scintillator positioned proximate to said source of particles and a two-dimensional optical detector positioned in optical communication with said scintillator; wherein each particle track corresponds to a particle path within said scintillator.

3. The method of claim 1, wherein said step of recording an image of a particle track with a particle track detector comprises:
    interacting a particle with a scintillator positioned proximate to said source, wherein said interaction generates a detectable optical signal along said particle track within said scintillator; and
    detecting at least a portion of said optical signal using a two-dimensional optical detector.

4. The method of claim 1, wherein said particle track detector comprises a microchannel plate positioned proximate to said source of particles, a light-emitting material positioned proximate to said microchannel plate and a two-dimensional optical detector positioned in optical communication with said light-emitting material; wherein each particle track corresponds to a particle path within said microchannel plate.

5. The method of claim 1, wherein said step of recording an image of a particle track with a particle track detector comprises:
    interacting a particle with a microchannel plate positioned proximate to said source, wherein said interaction generates electrons along said particle track within said microchannel plate, wherein said generated electrons are amplified within said microchannel plate and directed onto a light-emitting material positioned proximate to said microchannel plate, wherein interactions between said electrons and said light-emitting material generate a detectable optical signal; and
    detecting at least a portion of said detectable optical signal using a two-dimensional optical detector.

6. The method of claim 5, wherein an amount of amplification of said generated electrons depends on a position of said particle track within said microchannel plate.

7. The method of claim 6, wherein an intensity of said detectable optical signal is proportional to said amount of amplification of said generated electrons, thereby permitting determination of said position of said particle track within said microchannel plate.

8. The method of claim 5, comprising the step of imaging said detectable optical signal from said light-emitting material onto said two-dimensional optical detector using a lens or lens system.

9. The method of claim 1, wherein said particle track detector comprises deep depletion CCD device or deep-deletion CMOS device positioned proximate to said source of particles; wherein each particle track corresponds to a particle path within a deep depletion region of said deep depletion CCD device or deep-deletion CMOS device.

10. The method of claim 1, wherein said step of recording an image of a particle track with a particle track detector comprises interacting a particle with a depletion region of a deep-depletion CCD detector positioned proximate to said source, wherein said interaction generates electron-hole pairs along said particle track within said depletion region of said deep-depletion CCD detector, wherein generated electrons from the electron-hole pairs are accelerated toward and accumulated within a two-dimensional array of active CCD wells of said deep-depletion CCD detector.

11. The method of claim 1, wherein said attributes of said particle track comprise one or more of a position of a start of said particle track, a direction of travel of a particle at a start of said particle track, and a total energy deposited by a particle along a particle track.

12. The method of claim 1, further comprising, for each of said particles, storing said attributes of said particle track as entries in an attribute list, 4D grid of bins, or a database.

13. The method of claim 1, wherein said step of reconstructing said 3D distribution of said source of particles comprises using a list-mode maximum-likelihood expectation-maximization algorithm.

14. The method of claim 1, wherein said step of reconstructing said 3D distribution of said source of particles comprises calculating a probability density function for each of a plurality of locations within said source of particles.

15. The method of claim 1, further comprising a step of administering said source of particles to a patient, subject or tissue, wherein said source of particles comprises a radiopharmaceutical.

16. The method of claim 1, further comprising a step of obtaining a white-light image of an exposed surface of a tissue sample containing said source of particles.

17. The method of claim 16, wherein said following steps are repeated for a plurality of depths within said tissue sample:
 a) repeating said recording, determining and storing steps, thereby generating attributes for each of said plurality of depths, and
 b) obtaining a white-light image of a surface of said tissue sample;
thereby obtaining white-light images of exposed surfaces of said plurality of depths within said tissue sample and wherein said attributes comprises attributes of a plurality of particle tracks for each of said plurality of depths within said tissue sample; said method further comprising a step of reconstructing a 3D distribution of said source of particles using said attributes of particle tracks for each of said plurality of depths within said tissue sample.

18. The method of claim 1, further comprising providing a visual display of said 3D distribution of said source of particles.

19. A method for imaging a source of particles within a tissue sample, the method comprising the steps of:
 recording images of a plurality of particle tracks with a particle track detector;
 determining attributes of said plurality of particle tracks from said images;
 storing said attributes of each of said plurality of particle tracks;
 repeating said detecting, determining and storing steps for a plurality of depths within said tissue sample, wherein said plurality of depths are obtained by removing one or more layers of said tissue sample and wherein removal of each layer of said tissue sample exposes a deeper surface of said tissue sample, thereby generating particle track attributes for a plurality of particles from said source at a plurality of depths within said tissue sample; and
 reconstructing a 3D image of said source of particles using said particle track attributes for a plurality of particles from said source at a plurality of depths within said tissue sample and said plurality of depths within said tissue sample.

20. The method of claim 19 comprising a method of imaging a 3D distribution of a radioactive agent in an in vivo or ex vivo tissue.

* * * * *